US000001487H

United States Statutory Invention Registration [19]

[11] Reg. Number: H1487

Wong et al.

[43] Published: Sep. 5, 1995

[54] BENZOATE DERIVATIVES OF TAXOL

[75] Inventors: Henry Wong, Durham; Terrence Doyle, Killingworth, both of Conn.

[73] Assignee: Bristol-Myers Squibb Company, New York, N.Y.

[21] Appl. No.: 128,949

[22] Filed: Sep. 29, 1993

Related U.S. Application Data

[63] Continuation of Ser. No. 879,661, May 6, 1992, abandoned.

[51] Int. Cl.[6] ..... C07D 413/00

[52] U.S. Cl. ..... 544/147; 544/333; 544/375; 549/220; 549/510

[58] Field of Search ..... 544/147, 337, 375; 546/196; 549/220, 510; 514/85, 232.8, 253, 320, 449

[56] References Cited

U.S. PATENT DOCUMENTS

| | | | |
|---|---|---|---|
| 4,623,486 | 11/1986 | Lombardino et al. | 514/212 |
| 4,814,470 | 3/1989 | Colin et al. | 514/449 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,059,699 | 10/1991 | Kingston et al. | 549/511 |
| 5,272,171 | 12/1993 | Ueda et al. . | |

FOREIGN PATENT DOCUMENTS

400971A2 12/1990 European Pat. Off. .

OTHER PUBLICATIONS

Neal F. Magri et al, "Modified Taxols, 2. Oxidation Products of Taxol," *Journal of Organic Chemistry,* 1986, vol. 51, pp. 797–802.

Neal F. Magri et al, "Modified Taxols, 4. Synthesis and Biological Activity of Taxols Modified in the Side Chain," *Journal of Natural Products,* 1988, vol. 51, No. 2, pp. 298–306.

David G. I. Kingston et al, "The Chemistry of Taxol, A Clinically Useful Anticancer Agent," *Journal of Natural Products,* 1990, vol. 53, No. 1, pp. 1–12.

H. M. Deutsch et al, "Synthesis of Congeners and Prodrugs. 3. Water–Soluble Prodrugs of Taxol with Potent Antitumor Activity," *Journal of Medicinal Chemistry,* 1989, vol. 32, No. 4, pp. 788–792.

Hans Bundgaard et al, "A Novel Solution–Stable, Water–Soluble Prodrug Type for Drugs Containing a Hydroxyl or an NH–Acidic Group," *Journal of Medicinal Chemistry,* 1989, vol. 32, pp. 2503–2507.

Ejvind Jensen et al, "Design of a water–soluble, solution–stable and biolabile prodrug of mentronidazole for parenteral administration: N–substituted aminomethylbenzoate esters," *International Journal of Pharmaceutics,* 1990, vol. 58, 143–153.

Kent L. Amsberry et al., "The Lactonization of 2′–Hydroxyhydrocinnamic Acid Amides: A Potential Prodrug for Amines," *Journal of Organic Chemistry,* 1990, vol. 55, pp. 5867–5877.

*Primary Examiner*—Donald P. Walsh
*Assistant Examiner*—Chrisman D. Carroll
*Attorney, Agent, or Firm*—William T. Han

[57] ABSTRACT

This invention relates to a compound of formula I

I or a pharmaceutically acceptable salt thereof, in which $R^2$ is a radical of the formula (Abstract continued on next page.)

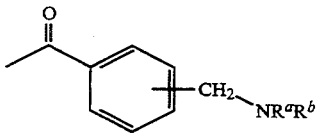

or

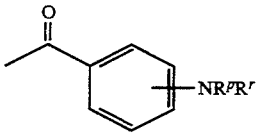

in which $R^a$ and $R^b$ are independently hydrogen or $C_{1-6}$ alkyl, said $C_{1-6}$ alkyl being optionally substituted with hydroxy, phosphono, phosphonooxy, carboxy or di($C_{1-6}$alkyl) amino; or $NR^aR^b$ together represents a radical of the formula

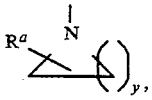

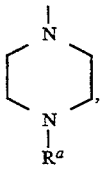

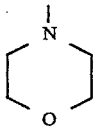

or

-continued

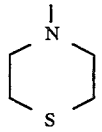

in which y is one to three, and $R^a$ is as defined above;

$R^p$ and $R^r$ are independently same or different $C_{1-6}$ alkyl;

$R^1$ is hydrogen or a radical Z of the formula

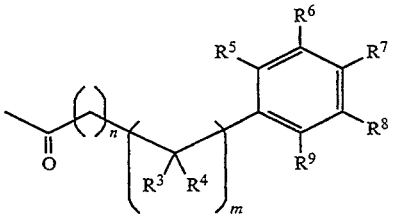

or

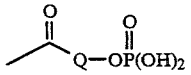

in which

Q is $—(CH_2)_f—$, optionally substituted with one to six same or different $C_{1-6}$ alkyl or $C_{3-6}$ cycloalkyl, or a carbon atom of said $—(CH_2)_f—$ radical may also be a part of $C_{3-6}$ cycloalkylidene;

$R^3$ and $R^4$ are independently hydrogen or $C_{1-6}$ alkyl, or $R^3$ and $R^4$ taken together with the carbon atom to which they are attached form $C_{3-6}$ cycloalkylidene;

$R^5$ is $—OC(=O)R$, $—OP=O(OH)_2$ or $—CH_2OP=O(OH)_2$, in which R is $C_{1-6}$ alkyl;

$R^6$, $R^7$, $R^8$ and $R^9$ are independently halogen, $C_{1-6}$ alkyl, $C_{1-6}$ alkoxy or hydrogen, but when $R^5$ is $—OC(=O)R$, one of $R^6$, $R^7$, $R^8$ or $R^9$ is $—OP=O(OH)_2$;

f is 2 to 6;

(Abstract continued on next page.)

n is O, and m is 1 or 0 when $R^5$ is $—CH_2OP—O(OH)_2$;

and n is 1 or 0, and m is 1 when $R^5$ is $—OC(=O)R$ or $—OP=O(OH)_2$.

Also provided by this invention are pharmaceutical formulations and a method for treating mammalian tumors with a compound of formula I.

17 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BENZOATE DERIVATIVES OF TAXOL

CROSS REFERENCE TO RELATED APPLICATION

This application is a continuation of U.S. Ser. No. 07/879,661, filed May 6, 1992, now abandoned.

BACKGROUND OF INVENTION

Taxol was first isolated from the stem bark of Western Yew, *Taxus brevifolia* Nut. (Taxaceae) and has the following structure (with the 2'- and 7- positions indicated)

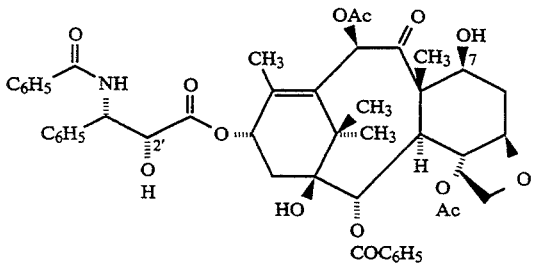

In ongoing clinical trials sponsored by the National Cancer Institute (NCI), taxol has shown promising results in fighting advanced cases of ovarian, breast, and other cancers. A recent review article in the Journal of National Cancer Institute provides an overview on its mechanism of action, toxicology, clinical results, etc. E. Rowinsky et al., *Taxol: A Novel Investigational Antimicrotubule Agent, J. Natl. Cancer Inst.*, 82: 1247–1259 (1990).

One serious problem associated with taxol is that the compound is only very slightly soluble in water and this low solubility has created significant problems in developing suitable pharmaceutical formulations useful for human therapy. Some formulations for i.v. infusion have been developed which primarily utilize cremophore EL(R) as the drug carrier to overcome low water solubility problems. Cremophore, however, is itself somewhat toxic which could cause idiosyncratic histamine release and anaphylactoid like response. Thus, any improvement to increase water solubility by chemical modification is highly desired.

In some instances, taxol has been made more water soluble through the derivatization of the 2'- and/or 7-hydroxy group with a hydrophilic group resulting in a bioreversible form known as a prodrug. Prodrugs have been shown to improve physicochemical (e.g. solubility, lipophilicity, etc.) and biological properties of many compounds. One approach to form a water soluble prodrug of a hydroxy containing molecule has been to derivatize the hydroxy group into an N-substituted-(aminomethyl)benzoate ester. See for example, Bundgaard et al., *J. Med. Chem.*, 32, pp 2507–2509 (1989); Jensen et al., *International Journal of Pharmaceutics*, 58, pp 143–153 (1990); U.S. Pat. No. 4,623,486, issued to Lombardino on Nov. 18, 1986.

We have now discovered that certain 2'-N-substituted-aminomethylbenzoate or 2'-N-substituted-aminobenzoate taxol derivatives, optionally substituted with a (phosphonooxyphenyl)alkanoyloxy, (phosphonooxy)alkanoyloxy, or [(phosphonooxyalkyl)phenyl]alkanoyloxy group on the (C)7-position of taxol, have respectable water solubility and good anti-tumor activities. Thus, it is the intention of this invention to provide novel 2'-N-substituted-aminomethylbenzoate or 2'-N-substituted-aminobenzoate taxol derivatives, with or without the 7-O-(phosphonooxyphenyl)alkanoyl, (phosphonooxy)alkanoyl, or [(phosphonooxyalkyl)phenyl]alkanoyl group, which are useful in treating mammalian tumors.

SUMMARY OF INVENTION

This invention relates to a compound of formula I

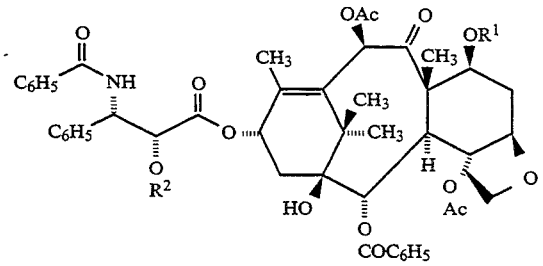

I or a pharmaceutically acceptable salt thereof, in which $R^2$ is a radical of the formula

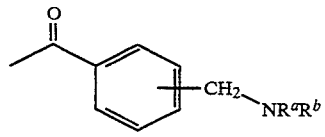

or

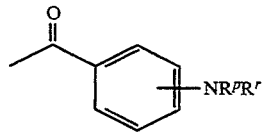

in which $R^a$ and $R^b$ are independently hydrogen or $C_{1-6}$ alkyl, said $C_{1-6}$ alkyl being optionally substituted with hydroxy, phosphono, phosphonooxy, carboxy or di($C_{1-6}$alkyl)amino; or $NR^aR^b$ together represents a radical of the formula

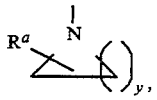

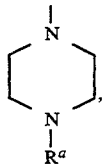

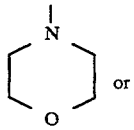

or

-continued

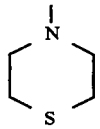

in which y is one to three, and $R^a$ is as defined above; $R^p$ and $R^r$ are independently same or different $C_{1-6}$ alkyl;

$R^1$ is hydrogen or a radical Z of the formula

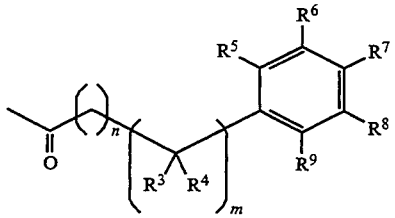

or

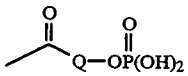

in which

Q is —$(CH_2)_f$—, optionally substituted with one to six same or different $C_{1-6}$ alkyl or $C_{3-6}$ cycloalkyl, or a carbon atom of said —$(CH_2)_f$— radical may also be a part of $C_{3-6}$ cycloalkylidene;

$R^3$ and $R^4$ are independently hydrogen or $C_{1-6}$ alkyl, or $R^3$ and $R^4$ taken together with the carbon atom to which they are attached form $C_{3-6}$ cycloalkylidene;

$R^5$ is —OC(=O)R, —OP=O$(OH)_2$ or —$CH_2$OP=O$(OH)_2$, in which R is $C_{1-6}$ alkyl;

$R^6$, $R^7$, $R^8$ and $R^9$ are independently halogen, $C_{1-6}$ alkyl, $C_{1-6}$ alkoxy or hydrogen, but when $R^5$ is —OC (=O)R one of $R^6$, $R^7$, $R^8$ $R^9$is —OP=O$(OH)_2$; f is 2 to 6;

n is O, and m is 1 or 0 when $R^5$ is —$CH_2$OP=O$(OH)_2$; and n is 1 or 0, and m is 1 when $R^5$ is —OC(=O)R or —OP=O$(OH)_2$.

This invention also provides pharmaceutical formulations and a method for treating mammalian tumors with a compound of formula I.

DETAILED DESCRIPTION OF THE INVENTION

This invention relates to a benzoate taxol derivative of formula I

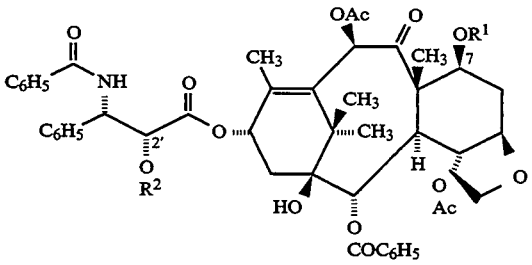

I or a pharmaceutically acceptable salt thereof, in which $R^2$ is a radical of the formula

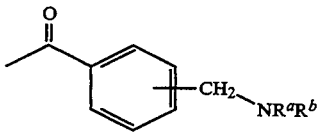

or

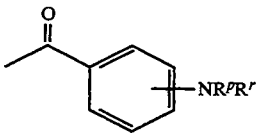

in which $R^a$ and $R^b$ are independently hydrogen or $C_{1-6}$ alkyl, said $C_{1-6}$ alkyl being optionally substituted with hydroxy, phosphono, phosphonooxy, carboxy or di($C_{1-6}$alkyl)amino; or $NR^aR^b$ together represents a radical of the formula

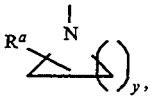

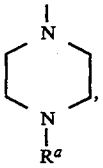

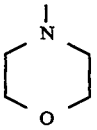

or

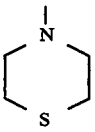

in which y is one to three, and $R^a$ is as defined above; $R^p$ and $R^r$ are independently same or different $C_{1-6}$ alkyl;

$R^1$ is hydrogen or a radical Z of the formula

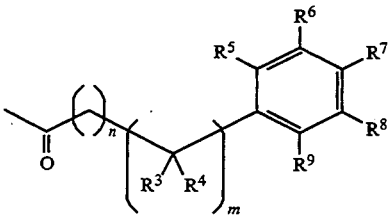

or

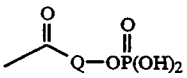

in which

Q is $-(CH_2)_f-$, optionally substituted with one to six same or different $C_{1-6}$ alkyl or $C_{3-6}$ cycloalkyl, or a carbon atom of said $-(CH_2)_f-$ radical may also be a part of $C_{3-6}$ cycloalkylidene; $R^3$ and $R^4$ are independently hydrogen or $C_{1-6}$ alkyl, or $R^3$ and $R^4$ taken together with the carbon atom to which they are attached form $C_{3-6}$ cycloalkylidene;

$R^5$ is $-OC(=O)R$, $-OP=O(OH)_2$ or $-CH_2OP=O(OH)_2$, in which R is $C_{1-6}$ alkyl;

$R^6$, $R^7$, $R^8$ and $R^9$ are independently halogen, $C_{1-6}$ alkyl, $C_{1-6}$ alkoxy or hydrogen, but when $R^5$ is $-OC(=O)R$, one of $R^6$, $R^7$, $R^8$ or $R^9$ is $-OP=O(OH)_2$; f is 2 to 6;

n is O, and m is 1 or 0 when $R^5$ is $-CH_2OP=O(OH)_2$; and n is 1 or 0, and m is 1 when $R^5$ is $-OC(=O)R$ or $-OP=O(OH)_2$.

Some compounds of formula I may form pharmaceutically acceptable metal and amine salts in which the cation does not contribute significantly to the toxicity or biological activity of the salt and are compatible with the customary pharmaceutical vehicles and adapted for oral or parenteral administration. These salts are also part of the present invention. Suitable metal salts include the sodium, potassium, calcium, barium, zinc, and aluminum salts. The sodium or potassium salts are preferred. Amines which are capable of forming stable salts may include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine, or the like amines.

Some compounds of formula I may also form pharmaceutically acceptable acid addition salts in which the anion does not contribute significantly to the toxicity of the salt and are compatible with the customary pharmaceutical vehicles and adapted for oral or parenteral administration. The pharmaceutically acceptable acid addition salts include the salts of compounds of formula I with mineral acids such as hydrochloric acid, hydrobromic acid, phosphoric acid and sulfuric acid, with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, p-toluenesulfonic acid, and the like acids.

Some compounds of the present invention may exist as zwitterionic forms. Pharmaceutically acceptable salts include not only pharmaceutically acceptable metal and amine salts and pharmaceutically acceptable acid addition salts but also zwitterionic forms, which are also within the scope of this invention.

In the instant application, the numbers in subscript after the symbol "C" define the number of carbon atoms a particular group can contain. For example, $C_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; $C_{3-6}$ cycloalkylidene refers to cyclopropylidene, cyclobutylidene, cyclopentylidene or cyclohexylidene; $C_{3-6}$ cycloalkyl refers to cyclopropyl, cyclobutyl, cyclopentyl, or cyclohexyl; $C_{1-6}$ alkyloxy (alkoxy) refers to straight or branched alkyloxy groups such as methoxy, ethoxy, n-propoxy, i-propoxy, n-butoxy, t-butoxy, n-pentyloxy, n-hexyloxy, or 3-methylpentyloxy, to name a few; di($C_{1-6}$alkyl)amino refers to amino with the same or different $C_{1-6}$ alkyl groups such as N-methyl-N-ethylamino, N,N-dimethylamino, N,N-diethylamino, N-hexyl-N-isopropylamino, etc.; phosphono refers to the radical $-P(=O)(OH)_2$; phosphonooxy refers to $-O-P(=O)(OH)_2$; and halogen refers to fluorine, chlorine, bromine, or iodine.

The synthesis of benzoate taxol derivatives of the instant invention can be accomplished by a wide variety of methods. In one embodiment, as shown in Scheme I, a compound of formula $I^1$, which is within the scope of formula I compounds, may be obtained by the steps comprising: [Step (1)] reacting taxol with chloromethylbenzoic anhydride of formula XXXV to afford a compound of formula XXX; and [Step (2)] reacting the compound of formula XXX with an secondary amine of the formula $$HNR^tR^u$$

wherein $R^t$ and $R^u$ are independently hydrogen or $C_{1-6}$ alkyl, said $C_{1-6}$ alkyl being optionally substituted with di($C_{1-6}$ alkyl)amino or hydroxy, or with a conventionally protected carboxy, phosphono or phosphonooxy group; or $NR^tR^u$ together represents a radical of the formula

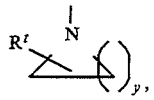

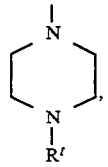

or

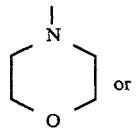

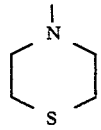

in which y is one to three and $R^t$ is as defined above. An additional step [Step (3)] of removing conventional carboxy, phosphonooxy or phosphono protecting group(s) is required if either or both $R^t$ and $R^u$ contain such protecting group(s).

As used herein, conventional carboxy protecting groups which can be employed in the present invention to block or protect the carboxylic acid function are well-known to those skilled in the art and, preferably, said groups can be removed, if desired, by methods which do not result in any appreciable destruction of the remaining portion of the molecule. Examples of such readily removable carboxy-protecting groups include moieties such as $C_{1-6}$ alkyl, diphenylmethyl (benzyhydryl), 2-naphthylmethyl, 4-pyridylmethyl, phenacyl, acetonyl, 2,2,2-trichloroethyl, silyl such as trimethylsilyl and t-butyldimethylsilyl, phenyl, ring substituted phenyl, e.g., 4-chlorophenyl, tolyl, and t-butylphenyl, phenyl $C_{1-6}$ alkyl, ring substituted phenyl $C_{1-6}$ alkyl, e.g., benzyl, 4-methoxybenzyl, 4-nitrobenzyl (p-nitrobenzyl), 2-nitrobenzyl (o-nitrobenzyl), and triphenylmethyl (trityl), methoxymethyl, 2,2,2-trichloroethoxycarbonyl, benzyloxymethyl, $C_{1-6}$ alkanoyloxy $C_{1-6}$ alkyl such as acetoxymethyl, propionyloxymethyl, $C_{2-6}$ alkenyl such as vinyl and allyl. Other suitable carboxy protecting groups well known in the art which have not been disclosed above can be found in "Protective Groups in Organic Synthesis", Theodora W. Greene and Peter G. M. Wuts, John Wiley & Sons, 2nd Edition, 1991, Chapter 5. Particularly advantageous carboxy protecting groups are benzyl, p-nitrobenzyl, o-nitrobenzyl, 2,4-dimethoxybenzyl, 4-methoxybenzyl, allyl, substituted allyl, t-butyl or diphenylmethyl (DPM).

A conventional phosphono or phosphonooxy protecting group can be $C_{1-6}$ alkyl, benzyl, allyl or 2,2,2-trichloroethyl, with a preferred phosphono protecting group being ethyl and a preferred phosphonooxy protecting group being benzyl, allyl or 2,2,2-trichloroethyl.

Step (1) of Scheme I is normally conducted in the presence of a strong base, such as LDA (lithium diisopropylamide), and in an inert solvent such as 1,4-dioxane, THF, DMF, diglyme, methylene chloride, or in the like solvent under reduced temperature. Moreover, all three methods (Methods A–C) in Example 28 may be adapted to make any of the positional isomers of a compound of formula XXX. The methods for making representative 2'-[(N-substituted-4-aminomethyl)benzoate]-taxols in Example 29 may be adapted to make other 2'-[(N-substituted-aminomethyl)benzoate]taxol derivatives.

As another example, when a compound of formula I in which $R^a$ and/or $R^b$ radical(s) contain(s) hydroxy group(s), the hydroxy group(s) may be reacted with (2,2,2-trichloroethyl)phosphorochloridate, and from the resulting product, 2,2,2-trichloroethyl group(s) may be removed to afford a compound of formula I which now contains phosphonooxy group(s). See Examples 31 and 32.

SCHEME I

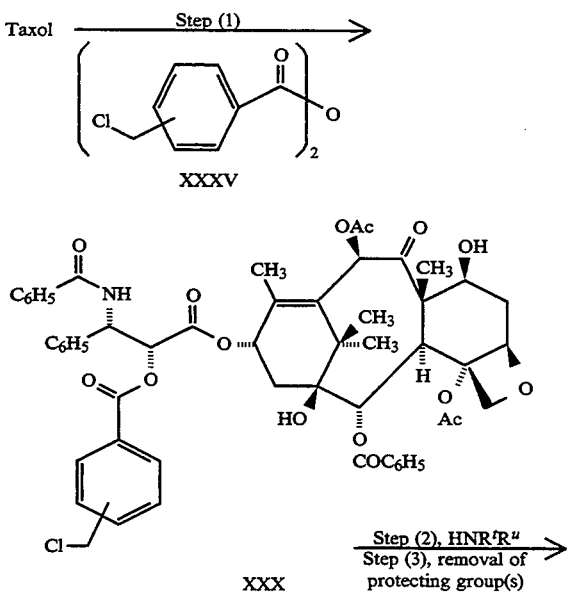

-continued

SCHEME I

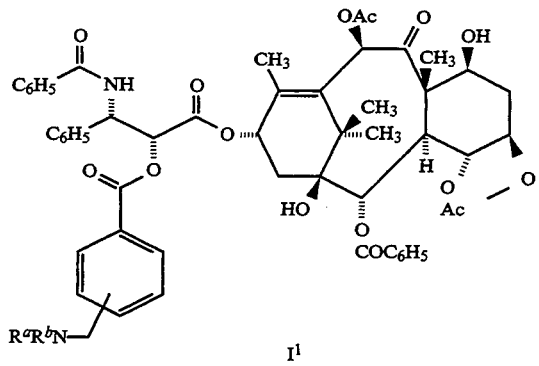

I[1]

A method of making a compound of formula I[2], which is further within the scope of formula I compounds, is depicted in Scheme II. In Step (1), a compound of formula XXX is reacted with an secondary amine of formula $HNR^{a'}R^{b'}$ wherein $R^{a'}$ and $R^{b'}$ are independently hydrogen or $C_{1-6}$ alkyl, said $C_{1-6}$ alkyl being optionally substituted with a conventionally protected carboxy, hydroxy, phosphonooxy, or phosphono group, or with a di($C_{1-6}$ alkyl-)amino group; or $NR^{a'}R^{b'}$ together represents a radical of the formula

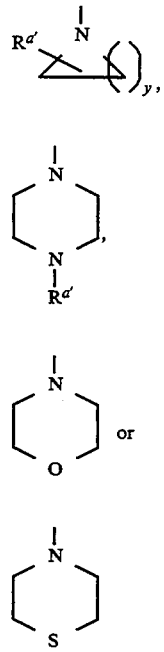

in which y is one to three and $R^{a'}$ is as defined above, to afford a compound of formula XXXI. Step (1) of Scheme II can be conducted in the same or substantially same manner as Step (2) of Scheme I. The 7-hydroxy of a compound of formula XXXI is subsequently acylated with an acid of formula IX or XXV

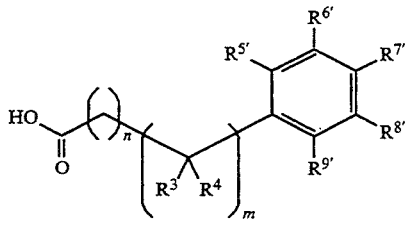

IX

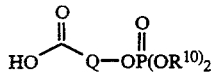

XXV (an acid of formula IX or XXV is esterified with the 7-hydroxy group of a compound of formula XXXI) to afford a compound of formula XXXII. In formula IX or XXV, $R^{5'}$ is —OC(=O)R, —OP=O($OR^{10}$)2 or —$CH_2$OP=O($OR^{10}$)$_2$; $R^{6'}$, $R^{7'}$, $R^{8'}$ and $R^{9'}$ are independently halogen, $C_{1-6}$ alkyl, $C_{1-6}$ alkoxy or hydrogen, but when $R^{5'}$ is —OC(=O)R, one of $R^{6'}R^{7'}$, $R^{8'}$ or $R^{9'}$ is —OP=O($OR^{10}$)$_2$; n is O, and m is 1 or 0 when $R^{5'}$ is —$CH_2$OP=O($OR^{10}$)$_2$; n is 1 or 0, and m is 1 when $R^{5'}$ is —OC(=O)R or —OP=O($OR^{10}$)$_2$; Q, R, $R^3$ and $R^4$ are as previously defined; and $R^{10}$ is a conventional phosphonooxy protecting group. In formula XXXII, $R^d$ is a radical of the formula

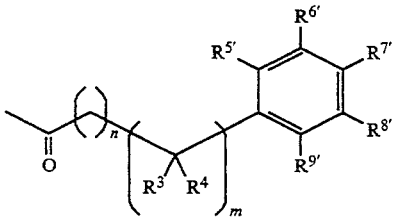

OR

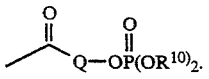

Subsequent removal of all protecting groups from a compound of formula XXXII in Step (3) affords a compound of formula $I^2$. When $R^{10}$ group is benzyl, it can be removed by catalytic hydrogenolysis.

As used herein, conventional hydroxy protecting groups are moieties which can be employed to block or protect the hydroxy function and they are well-known to those skilled in the art. Preferably, said groups are those which can be removed by methods resulting in no appreciable destruction to the remaining portion of the molecule. Examples of such readily removable hydroxy protecting groups include chloroacetyl, methoxymethyl, 2,2,2-trichloroethyloxymethyl, 2,2,2-trichloroethyloxycarbonyl, tetrahydropyranyl, tetrahydrofuranyl, t-butyl, benzyl, p-nitrobenzyl, p-methoxybenzyl, diphenylmethyl, trialkylsilyl, triphenylsilyl, and the like. A particularly advantageous protecting group for the 2'-hydroxy group of taxol is benzyloxycarbonyl, which can be removed conveniently by catalytic hydrogenolysis. Other suitable protecting groups which may be used are found in Chapter 2 of "Protecting Groups in Organic Synthesis", Second Ed., by Theodora W. Greene and Peter G. M. Wuts (1991, John Wiley & Sons).

The art of acylating a hydroxy group with a carboxylic acid is well known in the art. Particularly useful to the present invention are those which employ dehydrating agents such as dicyclohexylcarbodiimide (DCC), alkyl chloroformate and triethylamine, pyridinium salts-$Bu_3N$, phenyl dichlorophosphate, DCC and an aminopyridine, 2-chloro-1,3,5-trinitrobenzene and pyridine, polyphosphate ester, chlorosulfonyl isocyanate, chlorosilanes, $MeSO_2Cl$-triethylamine, $Ph_3P$-$CCl_4$-triethylamine, or N,N'-carbonyldiimidazole, to name a few. References to these reagents can be found in "Advanced Organic Chemistry", 3rd Ed., by Jerry March, pp 348–351 (1985, John Wiley & Sons). More particularly advantageous dehydrating system is comprised of DCC and 4-dimethylaminopyridine (4-DMAP).

A compound of formula $I^3$, which is within the scope of compounds of formula I, may be made by acylating the 2'-hydroxy group of taxol with an acid of formula XXXIV [Step (1), Scheme III]. Subsequent acylation of the 7-hydroxy group with an acid of formula XXV or IX in Step (2) generates a compound of formula XXXIII. Removal of all protecting groups from a compound of formula XXXIII affords a compound of formula $I^4$, which is further within the scope of formula I compounds.

SCHEME II

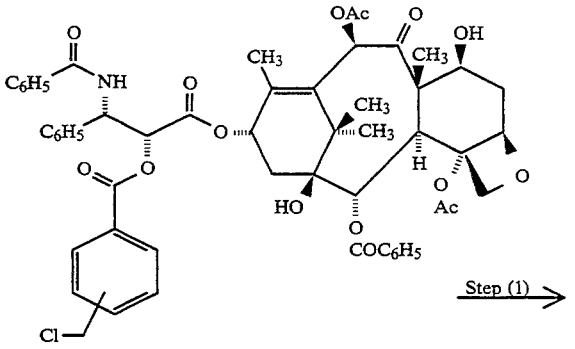

XXX

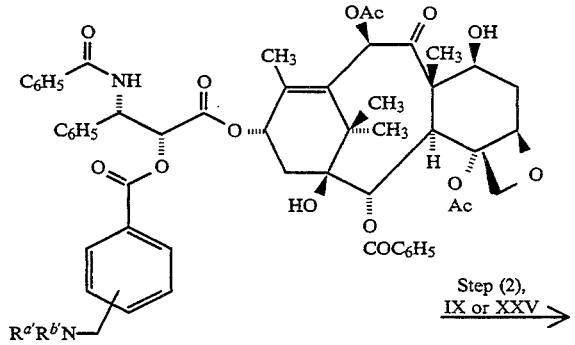

XXXI

-continued

SCHEME II

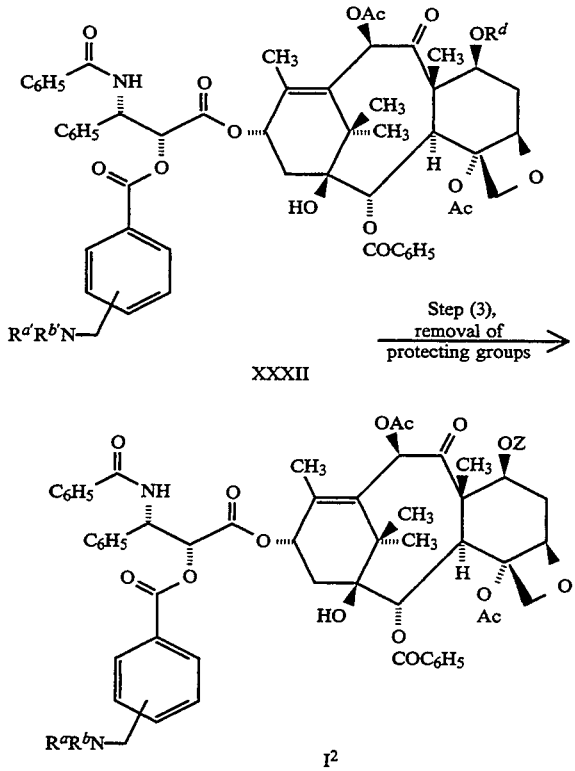

Any person skilled in the art would appreciate that when the removal of a conventional phosphonooxy protecting group $R^{1'}$ or a conventional phosphono protecting group in the above reaction Schemes (I–III) is conducted in the presence of an appropriate amount of base, the corresponding salt of the phosphonooxy or phosphono group can be obtained. For example, the presence of sodium bicarbonate during the removal affords the sodium salt.

The synthesis of acids of formula IX can be made by a wide variety of methods. For example, as a matter of illustration, synthesis of an acid of formula IX′, which is within the scope of the acids of formula IX, may be made by the sequence of steps as shown in Scheme A. In the Scheme, $R^{6'}$, $R^{7'}$, $R^{8'}$, and $R^{9'}$ preferably are independently hydrogen or $C_{1-6}$ alkyl; R, $R^3$ and $R^4$ are as previously defined.

The methods described by Amsberry et al., *Journal of Organic Chemistry,* 55, pp 5867–5877 (1990), for making certain compounds of formula III and IV in which $R^{6'}$and $R^{8'}$ are hydrogen, $R^{7'}$ is methyl or hydrogen, and $R^{9'}$ is methyl may be adapted to make additional compounds of formula III and IV. More specifically, Step (a) involves acid promoted transesterification of an acrylic acid ester with a phenol derivative of formula II and subsequent ring cyclization to afford a compound of formula III. The reaction is usually conducted in an inert organic solvent such as benzene, toluene or xylene, and the preferred catalyst is concentrated sulfuric acid. The reaction is normally conducted at an elevated temperature, preferably at or above the boiling point of benzene.

SCHEME III

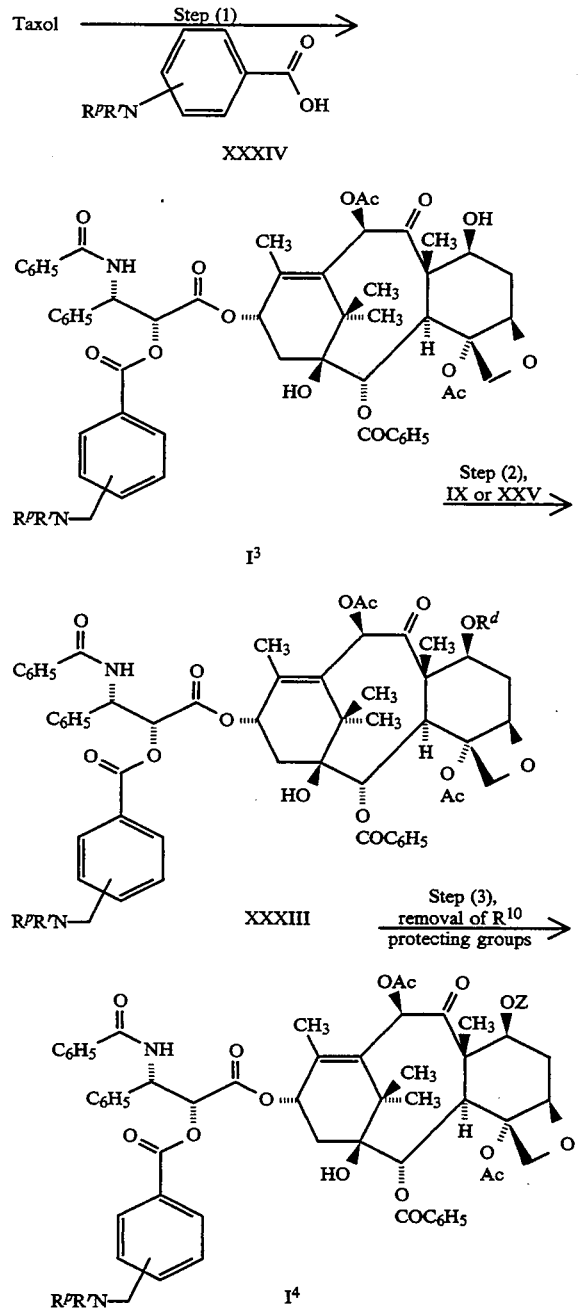

In Step (b), a lactone of formula III is being reduced. The reduction is normally conducted in an inert solvent such as 1,4-dioxane, diglyme, tetrahydrofuran (THF) or diethyl ether. A suitable reducing agent is lithium aluminum hydride. Other metal aluminum hydrides known to reduce lactones to alcohols may be employed as well.

Step (c) involves the protection of the free alkylhydroxy group in a compound of formula IV to afford a compound of formula V in which $R^{12}$ is a conventional hydroxy protecting group. Some examples of conventional hydroxy protecting groups are cited above. Here, a more desirable group for $R^{12}$ is t-butyldimethylsilyl. The attachment of t-butyldimethylsilyl group on a hydroxy group can be accomplished by reacting the hydroxy group with t-butyldimethylsilyl chloride in an inert solvent such as diethyl ether, 1,4-dioxane, diglyme, chloroform, DMF, THF, or methylene chloride, and also in the presence of an amine base such as imidazole, 4-dimethylaminopyridine, or triethylamine, N,N-diisopropylethylamine, or any other tri($C_{1-6}$)alkylamines.

In Step (d), the phenolic hydroxy group of a compound of formula V is phosphorylated with a compound of formula XXIV to afford a compound of formula VI in which $R^{10}$ is a phosphonooxy protecting group defined above. Here, a preferred $R^{10}$ radical is benzyl. As an example, the addition of dibenzylphosphono group is effected by reacting a phenolic salt of a compound of formula V with tetrabenzylpyrophosphate that in turn can be made from dibenzylphosphate and at least 0.5 equivalent of DCC. Step (d) is normally conducted in an inert aprotic solvent, such as 1,4-dioxane, diglyme, DMF or THF. The cation of the phenolic salt of a compound of formula V can be sodium, potassium, lithium, calcium, benzyltriethylammonium or tetraethylammonium, tetrabutylammonium or any other tetra($C_{1-6}$)alkylammonium. The formation of the phenolic salt can be effected by removing the phenolic proton by a base such as potassium carbonate, potassium hydroxide, potassium hydride, sodium hydride, sodium hydroxide, sodium carbonate, or a quaternary ammonium hydroxide such as tetrabutylammonium hydroxide or benzyltriethylammonium hydroxide.

In Step (e), the hydroxy protecting group $R^{12}$ is removed. When $R^{12}$ is t-butyldimethylsilyl, fluoride ion or mineral acid in alcohol may be used for its removal. The source of the fluoride ion can be from tetrabutylammonium fluoride. The removal with fluoride is conducted in an inert solvent such as THF, methylene chloride, 1,4-dioxane, DMF, chloroform, or in the like inert solvent; and preferably the reaction medium is buffered by a weak acid such as acetic acid. An example of mineral acid in alcohol is hydrochloric acid in isopropanol.

Step (f) entails the oxidation of the hydroxy group to the aldehyde group. A wide array of reagents are available for oxidizing a primary alcohol to an aldehyde, which may also be used to effect Step (f). Some examples include: dipyridine Cr(VI) oxide (Collin's reagent), pyridinium chlorochromate (PCC), pyridinium dichromate (PDC), ceric ammonium nitrate (CAN), $Na_2Cr_2O_7$ in water, N-iodosuccinimide and $Bu_4N^+I^-$, $Ag_2CO_3$-on-celite, N-methylmorpholine-n-oxide, a Ru complex, etc. References to the aforementioned reagents and to some other reagents for the oxidation can be found in such text as "Advanced Organic Chemistry", 3rd Ed., by Jerry March, pp 1057–1060 and 1081–1082 (1985, John Wiley & Sons). A preferable reagent for Step (f) is pyridinium chlorochromate (PCC) in methylene chloride. Step (g) involves a further oxidation of an aldehyde of formula VIII into an acid of formula IX'. Many reagents are known to convert an aldehyde to an acid. Some examples include: potassium permanganate, $Ag_2O$-water, m-chloroperbenzoic acid, Jones reagent (chromic and sulfuric acid in water), etc. The oxidation in Step (g) is preferably done by using the Jones reagent in acetone.

In a more preferred embodiment, a compound of formula IV can be directly converted to a compound of formula VII by employing the method specified above for Step (d). Furthermore, a compound of formula VII can be directly converted to a compound of formula IX' with the Jones reagent.

As another example, the synthesis of acids of formula IX", within the scope of formula IX compounds, can be made by a series of steps as shown in Scheme B. In the Scheme, $R^{6'}$, $R^{7'}$, and $R^{9'}$ preferably are independently hydrogen or $C_{1-6}$ alkyl; R, $R^3$ and $R^4$ are as defined previously. In Step (a), a quinone of formula X is reduced to a hydroquinone of formula XI by a standard quinone reduction method such as by employing sodium hydrosulfite. The annulation in Step (b) can be effected using the same or substantially the same condition described for Step (a) of Scheme A. The phenolic hydroxy group in a compound of formula XII is protected in Step (c) to afford a compound of formula XIII. A suitable phenol protecting group $R^{11}$ for the purpose of Step (c) is benzyl. Other well-known phenol protecting groups, such as those enumerated in pp. 144–170 of "Protecting Groups in Organic Synthesis", Second Ed., by Theodora W. Greene and Peter G. M. Wuts (1991, John Wiley & Sons), may also be used. The reduction in Step (d) can be conducted in the same or substantially the same manner as described for Step (b) of Scheme A. The protection of the alkyl hydroxy group in a compound of formula XIV with $R^{12}$ which has the meaning defined earlier, is conducted in the same or substantially the same way as described for Step (c) in Scheme A. The phenolic hydroxy group in a compound of formula XV is subsequently acylated in Step (f). The acylation methodologies which may be useful to the instant invention have been described hereinabove. In addition, acylation using a carboxylic anhydride of the formula $(RC{=}O)_2O$ can also be particularly useful for Step (f). In Step (g), the phenolic hydroxy protecting group $R^{11}$ is removed. When $R^{11}$ is benzyl it can be removed by catalytic hydrogenolysis. In Step (h), the conversion of a compound of formula XVII to a compound of formula XVIII can be effected in the same or substantially the same way as described for Step (d) of Scheme A. A preferred $R^{10}$ radical is again benzyl. The removal of $R^{12}$ hydroxy protecting group from a compound of formula XVIII can be carried out in the same or substantially same manner as described for Step (e) of Scheme A. The oxidation of the alcohol group to the carboxylic group in Step (j) can be done with the Jones reagent.

As a further example, the synthesis of acids of formula IX''' within the scope of formula IX compounds, can be made by a series of steps as shown in Scheme C. In the Scheme, $R^{6'}$, $R^{7'}$, $R^{8'}$, and $R^{9'}$ preferably are independently hydrogen or $C_{1-6}$ alkyl. The same or substantially the same reaction conditions described for Steps (c) and (e) of Scheme A can be employed to effect Steps (a) and (c), respectively, of Scheme C. For making a compound formula XXII in which $R^{10}$ is allyl or benzyl, a compound of formula XXI may be reacted with bis(allyloxy)(diisopropylamino)phosphine or dibenzyloxy(diisopropylamino)phosphine in the presence of a base, such as 1H-tetrazole; and the resulting addition product is subsequently oxidized, for example by m-chloroperbenzoic acid. The oxidation of Step (d) can be accomplished with the Jones reagent.

The synthesis of acids of formula XXV can be achieved by a wide array of methods. For example, as a matter of illustration, a series of steps in Scheme D can be used to make a compound of formula XXV' in which q equals 2 to 6, which are within the scope of formula XXV compounds. In the Scheme, one hydroxy group of a diol of formula XXVI is protected with the earlier defined $R^{12}$ radical to afford a compound of formula XXVII. A phosphonooxy group protected with $R^{10}$ radicals can be introduced by the same or substantially the same method that was described for Step (b) of Scheme C. The same or substantially the same method of Step (e) of Scheme A can be used to remove $R^{12}$ from a compound of formula XXVIII. Oxidation of a compound of formula XXIX using the Jones reagent affords a formula XXV′ compound.

The structural formulae as drawn herein are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

SCHEME A

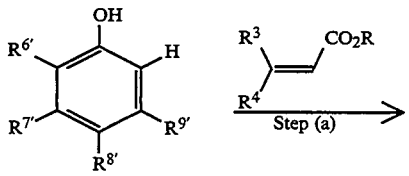

II

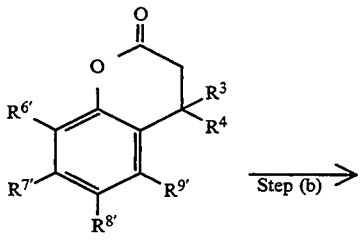

III

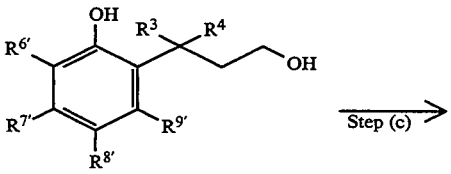

IV

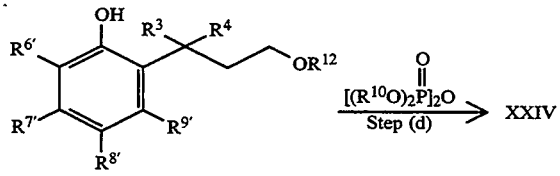

V

-continued

SCHEME A

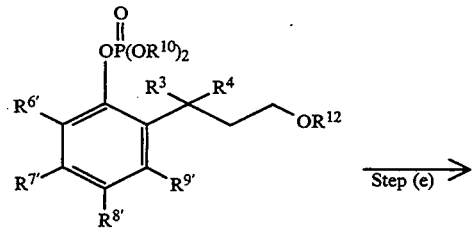

VI

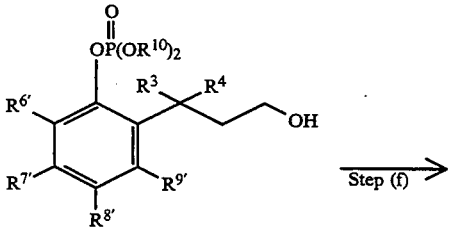

VII

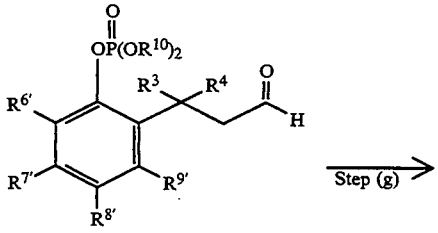

VIII

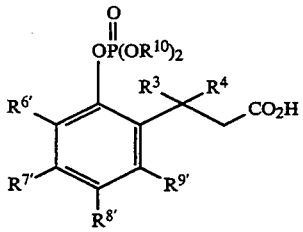

IX′

SCHEME B

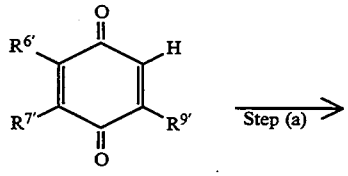

X

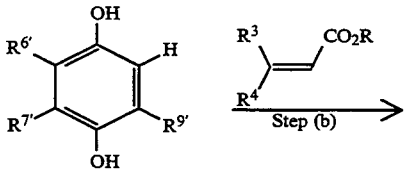

XI

-continued
SCHEME B
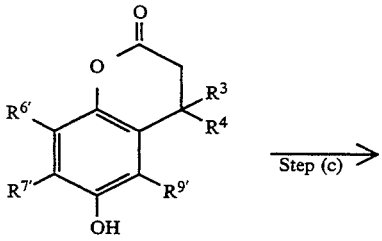
XII
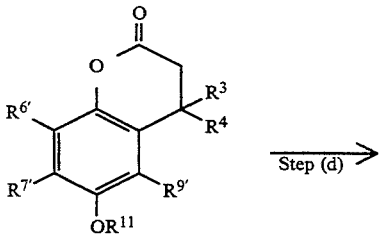
XIII
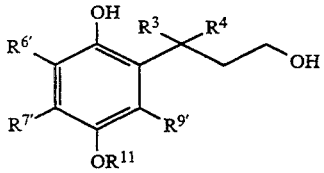
XIV
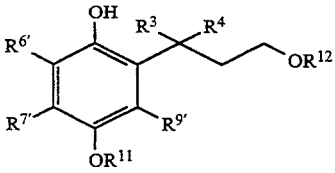
XV
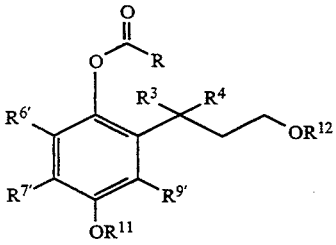
XVI
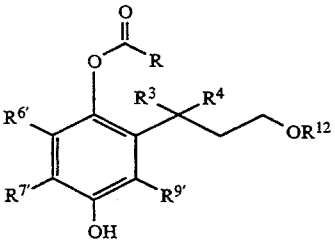
XVII
-continued
SCHEME B
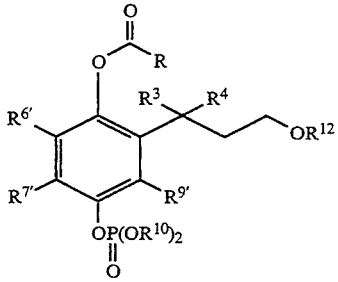
XVIII
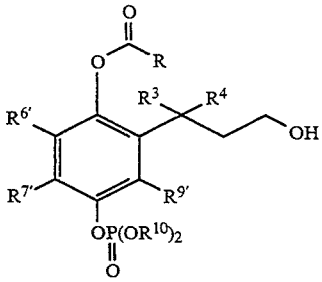
XIX
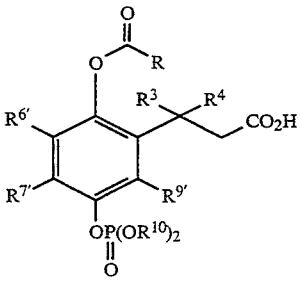
IX''
SCHEME C
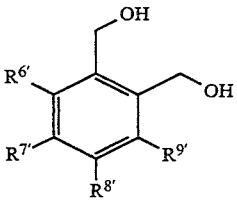
XX
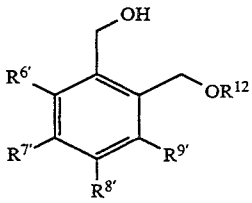
XXI -continued

SCHEME C

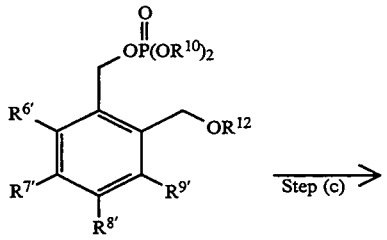

XXII

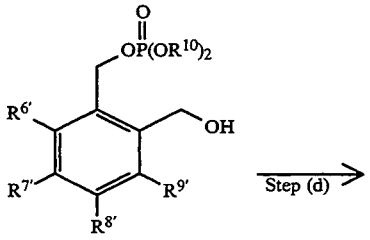

XXIII

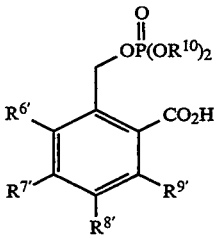

IX'''

SCHEME D

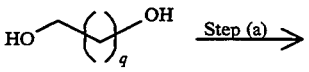

XXVI

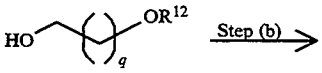

XXVII

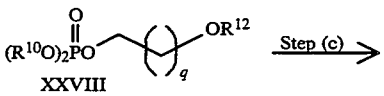

XXVIII

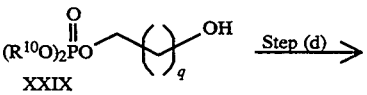

XXIX

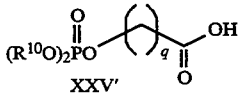

XXV'

DESCRIPTION OF SPECIFIC EMBODIMENTS

The specific examples which follow illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are:

| | |
|---|---|
| MS | Mass spectrometry |
| HRMS | High resolution mass spectrometry |
| DMF | Dimethylformamide |
| Ac | Acetyl |
| DMSO | dimethyl sulfoxide |
| Ph | phenyl |
| Ar | aryl |
| DCI | desorption chemical ionization |
| Y | yield |
| v/v | volume/volume |
| FAB | fast atom bombardment |
| NOBA | m-nitrobenzylalcohol |
| Rt | retention time |
| min | minute(s) |
| h | hour(s) |
| tlc | thin layer chromatography |
| tBu | tertiarybutyl |
| i-PrOH | isopropylalcohol |
| Cbz | Benzyloxycarbonyl |
| Bz (when used with a taxol structure) | Benzoyl |

In the examples that follow, hexane and hexanes may be used interchangeably.

EXAMPLE 1

4,4,5,7-Tetramethyl-3,4-dihydrocoumarin (IIIa)

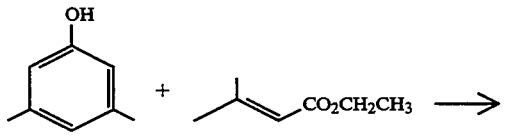

IIa

-continued

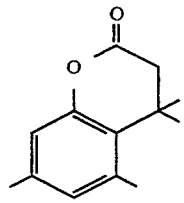

IIIa 3,5-Dimethylphenol (IIa) (3.2 g, 26.2 mmol), ethyl 3,3-dimethylacrylate (5 mL, 36 mmol, 1.4eq.) and concentrated sulfuric acid (1.5 mL) were dissolved in anhydrous benzene (30 mL), and the reaction mixture was heated to reflux for 2 h. The reaction mixture was cooled to room temperature and washed successively with water (2×40 mL), 5% aqueous $NaHCO_3$ solution (2×20 mL), brine (2×20 mL) and dried over anhydrous sodium sulfate. After filtering off the desiccant, the solvent was removed under vacuum to obtain dark brown gummy material. To this gummy material was added anhydrous ether (5 mL) and boiled for 2 min on a steam bath. The title compound, IIIa, (3.34 g, 16.4 mmol, Y: 62.4%) was crystallized out from the mixture upon cooling in an ice bath: mp, 95.8°–96.3° C.; $^1$H-NMR (300 MHz, acetone-$d_6$) δ ppm: 1.41 (6H, s, 4,4-$Me_2$), 2.24 (3H, s, 5-Me), 2.46 (3H, s, 7-Me), 2.61 (2H, s, 3 -$H_2$), 6.68 (1H, s, Ar-H), 6.76 (1H, s, Ar-H ); MS (Isobutane-DCI):m/e 205 $(M+H)^+$; IR (KBr) ν max: 1770, 1250, 1190, 870 $cm^{-1}$.

Anal. calcd for $C_{13}H_{16}O_2O$: C, 76.45; H, 7.90.
Found: C, 76.63; H, 7.83.

EXAMPLE 2

3-(2′-Hydroxy-4′,6′-dimethylphenyl)-3,3-dimethylpropanol (IVa)

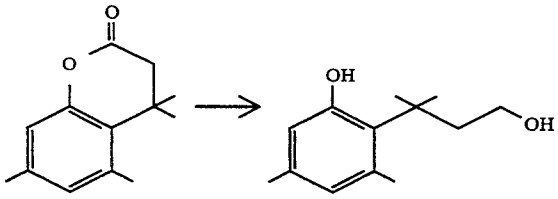

IIIa IVa

A solution of compound IIIa (27 g, 132.2 mmol) in dry tetrahydrofuran (THF, 100 mL) was added dropwise to a stirred suspension of 95% lithium aluminum hydride (LAH, 5.3 g, 132.5 mmol) in dry THF (250 mL) in 30 min period, so that the temperature did not rise for the suspension to reflux. The reaction mixture was stirred vigorously using a mechanical stirrer for 30 min. The excess of LAH was quenched with 10% aqueous HCl solution (15 mL). The insoluble material was filtered off and washed with EtOAc. The solvent was evaporated in vacuo from the combined filtrate and EtOAc washing. The residue, thus obtained, was taken into EtOAc (150 mL). The ethyl acetate layer was washed with brine (2×50 mL) and dried over anhydrous sodium sulfate. The desiccant was filtered off and the filtrate was concentrated in vacuo to obtain a gummy material. To this gummy material was added hexane/acetone (20 mL, 9:1, v/v) and boiled for 2 min on a steam bath. The title compound, IVa, (23.3 g, 111.9 mmol, Y:84.6%) crystallized out from the mixture upon cooling in an ice bath: mp, 116°–117° C.; $^1$H-NMR (300 MHz, acetone-$d_6$) δ ppm: 1.52 (6H, s, 3,3-$Me_2$), 2.1 (3H, s, 6′-Me), 2.17 (2H, t, J=7.7 Hz, 2-H2), 2.43 (3H, s, 4′-Me), 3.14 (1H, t, J=5.2 Hz, 1-OH, exchanged with $D_2O$), 3.39–3.45 (2H, m, 1-$H_2$), 6.37 (1H, s, Ar-H), 6.49 (1H, s, Ar-H), 7.98 (1H, s, 2′-OH, exchanged $D_2O$); MS (Isobutane-DCI): m/e 209 $(M+H)^+$; IR (KBr) ν max: 3510, 3230, 1310, 850 $cm^{-1}$.

Anal. calcd for: $C_{13}H_{20}O_2$: C, 74.97; H, 9.68.
Found: C, 75.35; H, 9.92.

EXAMPLE 3

1-O-t-Butyldimethylsilyl-3-(2′-hydroxy-4′,6′-dimethylphenyl)-3,3-dimethylpropanol (Va)

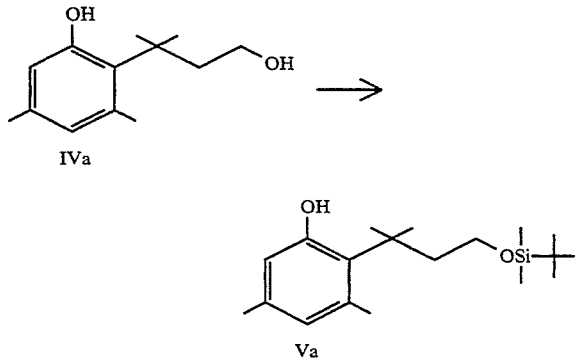

IVa Va

A mixture of compound IVa (6 g, 28.8 mmol), t-butyldimethylsilyl chloride (5.2 g, 34.5 mmol, 1.2 eq.), and imidazole (4.9 g, 71.97 mmol, 2.5 eq.) in anhydrous DMF (30 mL) was stirred overnight at room temperature. The reaction mixture was diluted with EtOAc (50 mL), washed with brine (5×40 mL) and dried over anhydrous sodium sulfate. The desiccant was filtered off and the filtrate was concentrated in vacuo to obtain a white solid which was recrystallized from hexane giving 8.9 g (27.59 mmol, Y: 96%) of the title compound, Va, as white crystalline material: top, 117°–118° C.; $^1$H-NMR (300 MHz, acetone-$d_6$) δ ppm: -0.15 (6H, s, Si-$Me_2$), 0.83 (9H, s, tBu), 1.53 (6H, s, 3,3-$Me_2$), 2.10 (3H, s, 6′-Me), 2.19 (2H, t, J=7.5 Hz, 2-$H_2$), 2.43 (3H, s, 4′-Me), 3.51 (2H, t, J=7.5 Hz, 1-$H_2$), 6.37 (1H, s, Ar-H), 6.50 (1H, s, Ar-H), 8.0 (1H, s, 2′-OH, exchanged with $D_2O$); MS (Isobutane-DCI): m/e 323 $(M+H)^+$; IR (KBr) ν max: 3308 (OH), 2856, 1614, 1390, 1260 $cm^{-1}$; UV (MeOH:$H_2O$, 1:1) λ max: 196 (ε $3.3\times10^4$), 284 nm (ε $1.9\times10^2$).

Anal. calcd for $C_{19}H_{34}O_2Si$: C, 70.75; H, 10.63.
Found: C, 70.52; H, 10.83.

EXAMPLE 4

1-O-t-Butyldimethylsilyl-3-[2′-(dibenzylphosphono)oxy-4′,6′-dimethylphenyl]-3,3-dimethylpropanol (VIa)

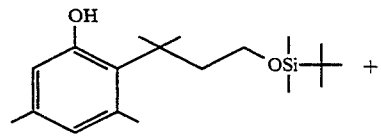

Va

-continued

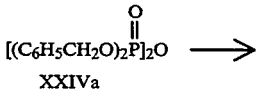

XXIVa

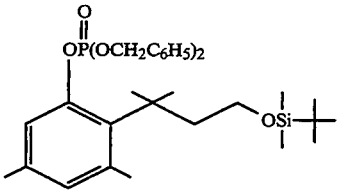

VIa

Sodium hydride (60% in mineral oil, 860 mg, 21.5 mmol, 1.2 eq. ) was washed with hexanes, dried under nitrogen and suspended in anhydrous DMF (70mL). To this suspension was added compound Va (5.8 g, 18 mmol), and the mixture was stirred in an oil bath at 65° C. for 5 min. To this warm reaction mixture was added tetrabenzylpyrophosphate (XXIVa) (14.5 g, 26.93 mmol, 1.5 eq.; pyrophosphate XXIVa was prepared from dibenzylphosphate and DCC) all at once. The reaction mixture was continued to be stirred at 65° C. for 10 min. Subsequently, it was diluted with EtOAc (300 mL), washed with brine (4×100 mL), and dried over anhydrous sodium sulfate. It was filtered and the filtrate was concentrated in vacuo to obtain compound VIa as a crude product which was purified on a silica gel column. The column was eluted with 10% EtOAc in hexanes to yield 10 g (17.16 mmol, Y:95%) of the title compound, VIa, as a gummy material: $^1$H-NMR (300 MHz, acetone-$d_6$) δ ppm: -0.57 (6H, s, Si-$Me_2$), 0.82 (9H, s, tBu), 1.52 (6H, s, 3,3-$Me_2$), 2.11 (2H, t, J=7.3 Hz, 2-$H_2$), 2.14 (3H, s, 6'-Me), 2.5 (3H, s, 4'-Me), 3.51 (2H, t, J=7.3 Hz, 1-$H_2$), 5.13–5.21 (4H, 2 ABq, $CH_2$Ph), 6.75 (1H, Ar-H), 7.12 (1H, s, Ar-H), 7.33–7.4 (10H, m); MS (Isobutane-DCI): m/e 583 $(M+H)^+$; IR ($NaC_1$ film) ν max: 1280 (P=O), 1260, 1018 (P-O) $cm^-$; UV (MeOH:-$H_2O$, 1:1) λ max: 196 nm (ε 3.95×103).

Anal. calcd for $C_{33}H_{47}O_5PSi$: C, 68.02; H, 8.13

Found: C, 68.19; H, 7.94.

EXAMPLE 5

3-[2'-(Dibenzylphosphono)oxy-4',6'-dimethylphenyl]-3,3-dimethylpropanol (VIIa)

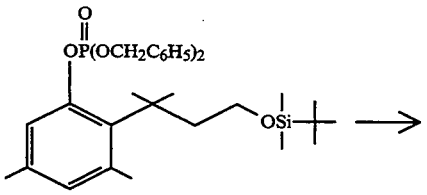

VIa

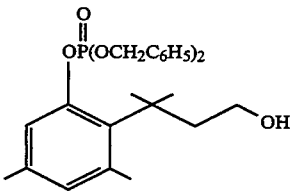

VIIa

To a solution of compound VIa (10 g, 17.2 mmol) in dry THF (250 mL) was added successively AcOH (6.2 mL, 108.3 mmol, 6.3 eq.) and tetrabutylammonium fluoride (TBAF) hydrate (13.5 g) at room temperature. The reaction mixture was stirred at room temperature for 3 days. The solvent was pumped off from the reaction mixture and the gummy residue was taken into EtOAc (300 mL), washed with brine (4×100 mL) and dried over anhydrous sodium sulfate. The desiccant was filtered off and the filtrate was concentrated in vacuo to obtain a crude product which was purified by silica gel column. The column was eluted with EtOAc/hexanes (1:1, v/v) to obtain 5.8 g (12.38 mmol, Y:72%) of the title compound, VIIa, as a gummy material: $^1$H-NMR (300 MHz, acetone-$d_6$) δ ppm: 1.51 (6H, s, 3,3-$Me_2$), 1.2 (2H, t, J=7.5 Hz, 2-$H_2$), 2.13 (3H, s, 6'-Me), 2.49 (3H, s, 4'-Me), 3.31 (1H, t, J=5.15 Hz, 1-OH, exchanged with $D_2O$), 3.39–3.46 (2H, m, 1-$H_2$), 5.17 (4H, ASq, $CH_2$ Ph), 6.74 (1H, s, Ar-H), 7.1 (1H, s, Ar-H), 7.3–7.42 (10H, m); MS (Isobutane-DCI): m/e 469 $(M+H)^+$; IR (NaCl film) ν max: 3442 (OH), 1275 (P=O), 1260, 1018 (P-O) $cm^{-1}$.

Anal. calcd for $C_{27}H_{31}O_5P$: C, 69.21; H,7.10.

Found: C, 68.94; H, 7.06.

EXAMPLE 6

3-[2'-(Dibenzylphosphono)oxy-4',6'-dimethylphenyl]-3,3-dimethylpropionaldehyde (VIIIa)

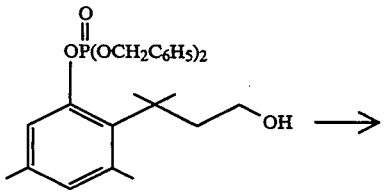

VIIa

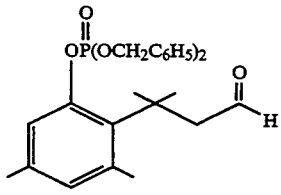

VIIIa

To a solution of compound VIIa (3.5 g, 7.5 mmol) in anhydrous $CH_2C_{12}$ (100 mL) was added pyridinium chlorochromate (PCC, 3.24 g, 15.03 mmol, 2 eq.) all at once at room temperature. The reaction mixture was allowed to be stirred at room temperature for 1 h. The volume of the reaction mixture was reduced to 10 mL by evaporating the solvent in vacuo. The resultant crude reaction product was purified on a silica gel column, being eluted with 40% EtOAc in hexanes to obtain 2.74 g (5.87 mmol, Y:78%) of the title compound, VIIIa, as a yellow viscous oil: 1H-NMR (300 MHz, acetone-$d_6$) δ ppm: 1.57 (6H, s, 3,3-$Me_2$), 2.14 (3H, s, 6'-Me), 2.51 (3H, s, 4'-Me), 2.91 (2H, d, J=2.3 Hz, 2-$H_2$), 5.11–5.23 (4H, 2 ABq, $CH_2$Ph), 6.78 (1H, s, At-H), 7.12 (1H, s, Ar-H), 7.35–7.39 (10H, m), 9.49 (1H, t, J=2.3 Hz, CHO); MS (Isobutane-DCI): m/e 467 $(M+H)^+$; IR (NaCl film ) ν max: 1740 (C=O), 1280 (P=O), 1020 (P-O) $cm^{-1}$; UV (MeOH:$H_2O$, 1:1) λ max:200 (ε 3.7×104), 264 nm (ε 3.6×102).

Anal. calcd for $C_{27}H_{31}O_5P$: C, 69.51; H, 6.70.

Found: C, 69.76; H, 6.73.

EXAMPLE 7

3-[2'-(Dibenzylphosphono)oxy-4',6'-dimethylphenyl]-3,3-dimethylpropionic acid (IXa)

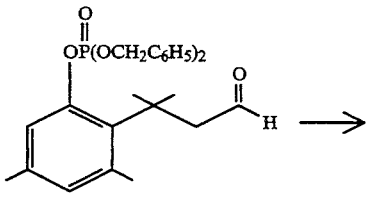

VIIIa

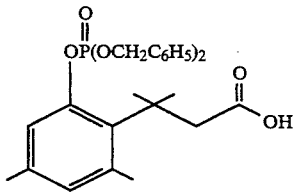

IXa

To a solution of compound VIIIa (1.46 g, 3.13 mmol) in acetone (40 mL) was added Jones reagent* (3 mL) at room temperature. The reaction mixture was stirred at room temperature for 20 min. The insoluble material was filtered off and the filtrate was concentrated in vacuo. The residue thus obtained was taken into EtOAc and purified on silica gel column, being eluted with EtOAc/$CH_2C_{12}$ (1:1, v/v) to obtain 1.0 g (2.07 mmol, Y:66%) of the title compound, IXa, as a gummy material: $^1$H-NMR (300 MHz, acetone-$d_6$) δ ppm: 1.6 (6H, s, 3,3-$Me_2$), 2.12 (3H, s, 6'-Me), 2.52 (3H, s, 4'-Me), 2.93 (2H, s, 2-$H_2$) 5.15–5.18 (4H, 2ABq, $CH_2Ph$), 6.72 (1H, s, Ar-H), 7.08 (1H, s, Ar-H), 7.33–7.4 (10H, m); MS (Isobutane-DCI: m/e 483 $(M+H)^+$; IR (NaCl film) ν max: 1715 (C=O), 1260 (P=O), 1020 (P-O) $cm^{-1}$; UV ( MeOH: HO, 1: 1 ) λ max: 202 (ε $4.2\times10^4$), 258 nm (ε $8.3\times10^2$).

Anal. calcd for $C_{27}H_{31}O_6P$: C, 67.21; H, 6.48.

Found: C, 66.75; H, 6.29.

*Note: The Jones reagent was prepared by dissolving $CrO_3$ (26.72 g) in "concentrated sulfuric acid (23 mL) and diluted with water to a volume of 100 mL" (see Fieser and Fieser "Reagents for Organic Synthesis" Vol 1, p 142, John Wiley, New York, 1967).

EXAMPLE 8

3-[2'-(Dibenzylphosphono)oxy-4',6'-dimethylphenyl]-3,3-dimethylpropanol (VIIa)

Sodium hydride (NaH, 1.20 g, 30 mmol; 60% in mineral oil, Aldrich) was washed with anhydrous hexanes, dried under dry nitrogen and suspended in anhydrous DMF (100 mL; Aldrich Sure Seal). To this suspension was added compound IVa (5.20 g, 25.0 mmol) and the mixture was heated at 65° C. for 5 min. To this warm mixture was added tetrabenzyl pyrophosphate (XXIVa) (20.2 g, 37.5 mmol) all at once. The reaction mixture was heated at 65° C. for 1½ h. The cooled reaction mixture was diluted with EtOAc (450 mL), washed with $H_2O$ (150 mL×3) and then with brine (150 mL). The organic phase was dried ($Na_2SO_4$) and concentrated. The residue was purified by silica column chromatography being eluted with 35% EtOAc in hexanes to obtain 4.70 g (10 mmol, Y: 40.1%) of the title compound, VIIa, as a gummy oil. This material was identical to the product obtained in Example 5 as determined by $^1$H-NMR (300 MHz, acetone-$d_6$).

EXAMPLE 9

3-[2'-(Dibenzylphosphono)oxy-4',6'-dimethylphenyl]-3,3-dimethylpropionic acid (IXa)

To a solution of the alcohol VIIa (4.90 g, 10.5 mmol) in acetone (75 mL) was added Jones reagent (10 mL) at room temperature. The reaction mixture was stirred at room temperature for 20 min. The insoluble material was filtered and the filtrate concentrated in vacuo. The residue was taken into EtOAc and purified by silica gel column chromatography, being eluted with 50% EtOAc in $CH_2C_2$ to obtain 3.20 g (6.64 mmol, Y: 63.5%) of the title compound, IXa as a yellowish oily solid: Rf 0.44 (50% EtOAc/hexane); $^1$H-NMR (300 MHz, acetone-$d_6$ indicated that this material was identical to the product obtained in Example 7.

EXAMPLE 10

1,4-Dihydroxy-2,6-dimethylbenzene (XIa)

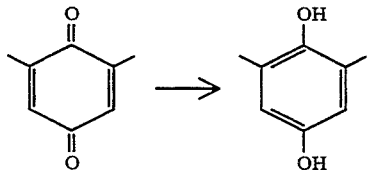

Xa XIa

A solution of 2,6-dimethyl-1,4-benzoquinone (Xa) (5.66g, 42 mmol, Aldrich) in $Et_2O$ (200 mL) was shaken vigorously in a separatory funnel with two 200 mL portions of aqueous sodium hydrosulfite solution (sodium dithionite, $Na_2S_2O_4$, 14.5 g, 83.3 mmol) until the $Et_2O$ layer turned bright yellow. The ether layer was washed with brine (200 mL×2), dried ($MgSO_4$) and concentrated in vacuo to obtain 4.865g (35.3 mmol, Y: 83.9%) of the title compound as a white solid: mp, 148°–150° C. (acetone-hexane) [mp reported by L. A. Carpino, S. A. Triolo, and R. A. Berglund in *J. Org. Chem.*, 54, 3303 (1989): 145°–148° C.]; Rf 0.47 (10% EtOAc in $CH_2Cl_2$); IR(KBr) 3312 $cm^{-1}$ (OH); $^1$H-NMR (300 MHz, acetone-$d_6$) δ ppm: 2.15 (6H, s, Me), 6.45 (2H, s, Ar-H), 6.58 (1H, s, OH), 7.47 (1H, s, OH); $^{13}$C-NMR (75 MHz, acetone-$d_6$) δ ppm: 16.84, 116.00, 126.45, 147.46, 151.54; MS (isobutane-DCI) m/e 139 ($MH^+$).

EXAMPLE 11

6-Hydroxy-4,4,5,7-tetramethylhydrocoumarin (XIIa)

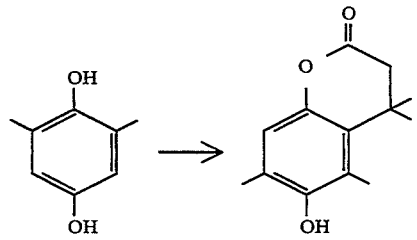

XIa XIIa

A mixture of 1,4-dihydroxy-2,6-dimethylbenzene (XIa) (4.83 g, 35 mmol), ethyl β,β-dimethylacrylate (5.38g, 42 mmol; Aldrich) and concentrated sulfuric acid (2 mL) in toluene (200 mL) was heated at reflux for 3.5 h. After the mixture had cooled, it was washed successively with $H_2O$ (200 mL×2), 5% aqueous $NaHCO_3$ solution (200 mL×2), and then with brine (200 mL). The toluene solution was dried ($MgSO_4$) and concentrated in vacuo. The residual solid was crystallized from toluene to obtain 4,637 g (21.1 mmol, Y: 60.2%) of the title compound as off-white solid: mp, 141°–142° [mp reported by K. L. Amsberry and R. T. Borchardt in *Pharmaceutical Res.*, 8, 323 (1991): 140°–142° C.]; Rf 0.67 (10% EtOAc in $CH_2Cl_2$); IR(KBr) 3418(OH), 1742 $cm^{-1}$ (lactone); $^1$H-NMR (300MHz, acetone-$d_6$) δ ppm: 1.43 (6H, s, gem-Me), 2.22 (3H, s, Ar-Me), 2.38 (3H, s, Ar-Me), 2.56 (2H, s, $CH_2$), 6.66 (1H, s, At-H), 7.19 (1H, s, OH); $^{13}$C-NMR (75 MHz, acetone-$d_6$) δ ppm: 15.12, 16.64, 27.94, 36.15, 46.56, 117.56, 124.49, 125.26, 129.79, 146.16, 151.45, 169.15; MS (isobutane-DCI) m/e 221 (MH+).

Anal. calcd for $C_{13}H_{16}O_3$: C, 70.89; H, 7.33.
Found: C, 71.21; H, 7.43.

EXAMPLE 12

6-Benzyloxy-4,4,5,7-tetramethylhydrocoumarin (XIIIa)

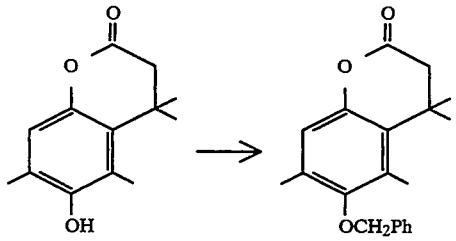

XIIa XIIIa

A mixture of hydroxyhydrocoumarin XIIa (1.10 g, 5 mmol), benzyl bromide (1.28 g, 7.5 mmol; Aldrich) and anhydrous potassium carbonate (1.38 g, 10 mmol) in anhydrous DMF (10 mL; Aldrich Sure Seal) was stirred under dry nitrogen atmosphere for 3 days. The mixture, diluted with EtOAc (30 mL) and $H_2O$ (10 mL), was washed successively with 2N hydrochloric acid (14 mL), $H_2O$ (10 mL), 5% aqueous $NaHCO_3$ solution (10 mL), and then with brine (15 mL). The EtOAc layer was dried ($Na_2SO_4$) and concentrated in vacuo to dryness. The resulting solid was triturated with hexane to obtain 1.359 g (4.38 mmol, Y: 87.7%) of the title compound as off-white solid: mp, 94°–96° C. (recrystallized from isopropyl alcohol); Rf 0.57 (30% EtOAc in hexane); IR(KBr) 1768 $cm^{-1}$ (lactone); $^1$H-NMR (300 MHz, $CDCl_3$) δ ppm: 1.43 (6H, s, gem-Me), 2.26 (3H, s, Ar-Me), 2.40 (3H, s, Ar-Me), 2.56 (2H, s, $CH_2$), 4.73 (2H, s, $OCH_2$), 6.76 (1H, s, At-H), 7.3–7.5 (5H, m, Ar-Hs); $^{13}$C-NMR (75 MHz, $CDCl_3$) δ ppm: 15.15, 16.54, 27.87, 35.78, 46.15, 74.85, 118.00, 128.38, 128.72, 129.12, 129.17, 130.31, 131.55, 137.88, 148.02, 153.44, 169.15; MS (isobutane-DCI) m/e 311 (MH+), 91.

Anal. calcd for $C_{20}H_{22}O_3$: C, 77.40; H, 7.15.
Found: C, 77.37; H, 7.13.

EXAMPLE 13

3-(2′-Hydroxy-5′-benzyloxy-4′,6′-dimethylphenyl)-3,3-dimethyl-1-propanol (XIVa)

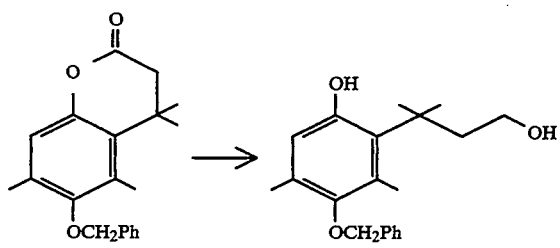

XIIIa XIVa

A solution of benzyloxyhydrocoumarin XIIIa (1.147 g, 3.70 mmol) in anhydrous THF (7 mL) was carefully added to a stirred suspension of $LiAlH_4$ (281 mg, 7.4 mmol) in anhydrous THF (15 mL). The mixture was stirred at room temperature under dry nitrogen atmosphere for 20 min and then heated at reflux for 30 min by which time the tlc (30% EtOAc in hexane) indicated that the reaction was complete. The mixture was cooled in an ice-bath and to this mixture was added carefully and successively EtOAc (15 mL), 6N hydrochloric acid (5 mL), and $H_2O$ (15 mL). The EtOAc layer was collected and the aqueous layer was extracted with EtOAc (25 mL). Both EtOAc layers were combined and washed successively with in hydrochloric acid (25 mL), saturated aqueous $NaHCO_3$ solution (25 mL), and brine. The EtOAc layer was dried ($Na_2SO_4$) and concentrated in vacuo to dryness to obtain 1.10 g (3.35 mmol, Y: 90.6%) of the title compound as white solid: top, 90°–91° C.; Rf 0.15 (30% EtOAc in hexane); IR(KBr) 3462, 3262, 1606 $cm^{-1}$; $^1$H-NMR (300 MHz, acetone-$d_6$) δ ppm: 1.58 (6H, s, gem-Me), 2.16 (3H, s, Ar-Me), 2.21 (2H, t, J=7.8 Hz, $CH_2$), 2.46 (3H, s, Ar-Me), 3.17 (1H, t, J=5 Hz, OH), 3.45–3.52 (2H, m, $CH_2O$), 4.69 (2H, s, $OCH_2Ph$), 6.55 (1H, s, Ar-H), 7.3–7.55 (5H, m, Ph-Hs), 7.85 (1H, s, Ar-OH); $^{13}$C-NMR (75 MHz, acetone-$d_6$) δ ppm: 16.47, 32.73, 41.00, 46.39, 61.15, 75.02, 118.03, 127.90, 129.01, 129.11, 129.46, 129.68, 131.86, 132.40, 139.68, 150.92, 153.88; MS(FAB/NOBA+-NaI+KI) m/e 353 (MK+), 337 (MNa+), 314 (M+), 229, 223.

Anal. calcd for $C_{20}H_{26}O_3$: C, 76.41; H, 8.34.
Found: C, 76.28; H, 8.25.

EXAMPLE 14

1-O-t-Butyldimethylsilyl-3-(5′-benzyloxy-4′,6′-dimethyl-2′-hydroxyphenyl)-3,3-dimethylpropanol (XVa)

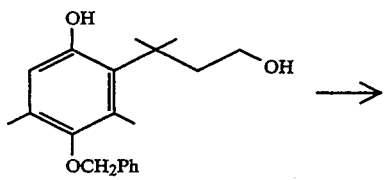

XIVa

-continued

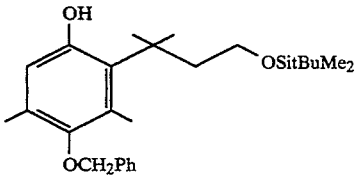

XVa

A mixture of diol XIVa (1.017 g, 3.10 mmol), t-butyldimethylsilyl chloride (561 mg, 3.72 mmol; Aldrich) and imidazole (527mg, 7.75 mmol) in DMF (5 mL; Aldrich, Sure Seal) was stirred at room temperature under nitrogen atmosphere for 18 h. This mixture was diluted with EtOAc (20 mL) and successively washed with $H_2O$ (15 mL×3) and brine (15 mL). The EtOAc phase was dried ($Na_2SO_4$) and concentrated in vacuo to give 1.38 g (3.16 mmol, Y: ≧100%) of the title compound as a crude oil: Rf 0.72 (30% EtOAc in hexane); IR (film) 3380 $cm^{-1}$(OH); $^1$H-NMR (300 $MH_z$, acetone-$d_6$) δ ppm: -0.03 (6H, s, $SiMe_2$), 0.84 (9H, s, SitBu), 1.56 (6H, s, gem-Me), 2.15 (3H, s, Ar-Me), 2.20 (2H, t, J=7.5 Hz, $CH_2$), 2.45 (3H, s, Ar-Me), 3.56 (2H, t, J=7.5 Hz, $CH_2OSi$), 4.67 (2H, s, $OCH_2Ph$), 6.54 (1H, s, Ar-H), 7.3–7.5 (5H, m, Ph-Hs), 7.88 (1H, s, Ar-OH); MS (isobutane-DCI) m/e 429 (MH+), 337, 297, 201.

EXAMPLE 15

1-O-t-Butyldimethylsilyl-3-(2'-acetoxy-5'-benzyloxy-4',6'-dimethylphenyl)-3,3-dimethylpropanol (XVIa)

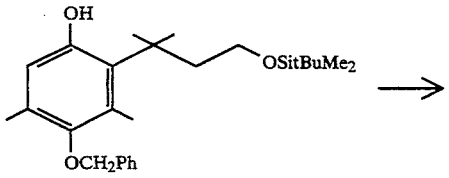

XVa

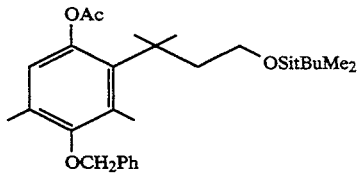

XVIa

To a solution of phenol XVa (1.38 g, 3.10 mmol; crude) in pyridine (2 mL; dried over NaOH) was added acetic anhydride (1 mL, 10.6 mmol) and the solution was stirred at room temperature for 15 h. The volatiles were evaporated in vacuo and the residue, diluted with $CH_2Cl_2$ (20 mL), was successively washed with $H_2O$ (15 mL ×2) and brine (15 mL). The $CH_2Cl_2$ phase was dried ($Na_2SO_4$) and concentrated in vacuo. The residue was purified by column chromatography ($SiO_2$, 100 g), being eluted with 12% EtOAc in hexane to obtain 1.24 g (2.64 mmol, Y: 85.2%) of the title compound as a clear oil: Rf 0.23 (10% EtOAc in hexane); IR (film): 1760 $cm^{-1}$ (OAc); $^1$H-NMR (300 MHz, $CDCl_3$) δ ppm: -0.03 (6H, s, $SiMe_2$), 0.83 (9H, s, SitBu), 1.47 (3H, s, Ar-Me), 2.05 (2H, t, J=7.5 Hz, $CH_2$), 2.23 (3H, s, Ar-Me), 2.25 (3H, s, OAc), 2.47 (3H, s, Ar-Me), 3.50 (2H, t, J=7.5 Hz, $CH_2OSi$), 4.72 (2H, s, $OCH_2Ph$), 6.58 (1H, s, Ar-H), 7.2–7.5 (5H, m, Ph-Hs); MS (isobutane-DCI) m/e 471 (MH+), 413 , 385 , 201.

Anal. calcd for $C_{28}H_{42}Si$: C, 71.45, H, 9.00.
Found: 71.47; H, 9.21.

EXAMPLE 16

1-O-t-Butyldimethylsily]-3-(2'-acetoxy-4',6'-dimethyl-5'-hydroxyphenyl)-3,3-dimethylpropanol (XVIIa).

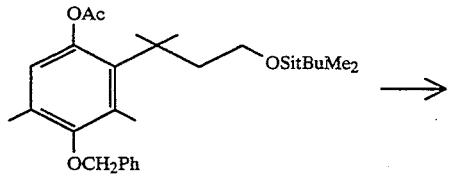

XVIa

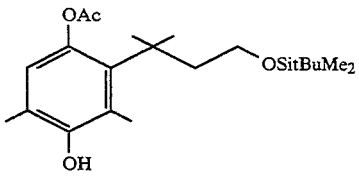

XVIIa

To a solution of benzyl ether XVIa (1.19 g, 2.53 mmol) in absolute EtOH (100 mL) was added 10% Pd-C (400 mg, Aldrich), and the mixture was stirred in a Parr apparatus under hydrogen atmosphere (30 psi) at room temperature for 2 h. The catalyst was removed by filtration through Celite and the filtrate was concentrated. The residue was purified by column chromatography ($SiO_2$, 15 g), being eluted with 20% EtOAc in hexane to obtain 863 mg (2.27 mmol, Y: 97.1%) of the title compound as white solid: mp, 87°–88° C. (recrystallized from EtOAc/hexane); Rf 0.34 (20% EtOAc in hexane); IR(KBr) 3490 (OH), 1734, 1232 $cm^{-1}$ (OAc); $^1$H-NMR (300 MHz, acetone-$d_6$); δ ppm: -0.03 (6H, s, $SiMe_2$), 0.84 (9H, s, tBu), 1.46 (6H, s, gem-Me), 2.05 (2H, t, J=7.5 Hz, $CH_2O$), 2.16 (3H, s, Ar-Me), 2.19 (3H, s, OAc), 2.40(3H, Ar-Me), 3.53 (2H, t, J=7.5 Hz, $CH_2O$), 6.50 (1H, s, Ar-H), 7.10 (1H, s, Ar-OH); MS (isobutane-DCI) m/e 381 (MH+), 323, 295, 201, 145.

Anal. calcd for $C_{21}H_{36}O_4Si$: C, 66.28; H, 9.54.
Found: C, 66.28; H, 9.83.

EXAMPLE 17

1–0-t-Butyldimethylsilyl-3-(2'-acetoxy-5'-dibenzylphosphonooxy-4',6'-dimethylphenyl)-3,3dimethylpropanol (XVIIIa)

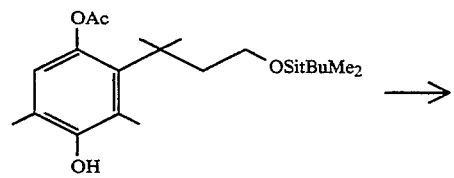

XVIIa

-continued

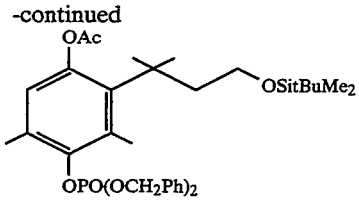

XVIIIa

NaH (120 mg, 3.0 mmol; 60% dispersion, Aldrich) was washed with anhydrous hexane to remove the oil. To a suspension of the residue in anhydrous DMF (10 mL; Aldrich Sure Seal) was added a solution of phenol XVIIa (760 mg, 2.0 mmol) in DMF (5 mL). The mixture was heated at 60°–70° C. under dry nitrogen atmosphere for 15 min and to this was added tetrabenzyl pyrophosphate (XXIVa) (1.61 g, 3.0 mmol). The mixture was continued to be heated at 60°–70° C. for 30 min. The mixture was subsequently cooled, diluted with EtOAc (30 mL), and successively washed with $H_2O$ (20 mL×3) and brine (20 mL). The organic phase was dried ($Na_2SO_4$) and concentrated. The residue was purified by column chromatography ($SiO_2$, 100 g), being eluted with 20% EtOAc in hexane to obtain 1.04 g (1.63 mmol, Y: 81.6%) of the title compound as an oil: Rf 0.23 (20% EtOAc in hexane); IR (film) 1760 $cm^{-1}$ (OAc); $^1$H-NMR (300 MHz, $CDCl_3$) 6 ppm: −0.04 (6H, s, $SiMe_2$), 0.83 (9H, s, tBu), 1.42 (6H, s, gem-Me), 2.00 (2H, t, J=7.5 Hz , $CH_2$), 2.24 (3H, s, Ar-Me), 2.25 (3H, s, OAc), 2.43 (3H., s, Ar-Me), 3.54 (2H, t, J=7.5 Hz, $CH_2OSi$), 5.03 (2H, s, $OCH_2Ph$), 5.06 (2H, s, $OCH_2Ph$), 6.55 (1H, s, Ar-H), 7.2–7.4 (10H, m, Ph-Hs); MS (isobutane-DCI) m/e 641 (MH+), 583,441.

Anal. calcd for $C_{35}H_{49}O_7PSi$: C, 65.61; H, 7.71.
Found: C, 65.68; H, 7.64.

EXAMPLE 18

3-(2′-Acetoxy-5-dibenzylphosphonooxy-4, 6′-dimethylphenyl)-3,3-dimethylpropanol (XIXa)

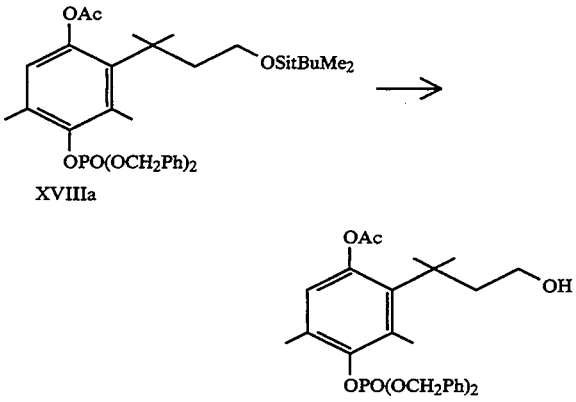

XVIIIa

XIXa

To a solution of silylether XVIIIa (960 mg, 1.5 mmol) in anhydrous THF (30 mL; distilled from benzophenone ketyl) was added HOAc (0.6 mL, 10.5 mmol; glacial) followed by tetrabutylammonium fluoride hydrate (1.59 g; Aldrich). The resultant mixture was stirred at room temperature for 1.5 h. The mixture was diluted with EtOAc (50 mL) and was successively washed with $H_2O$ (×2) and brine. The organic phase was dried ($Na_2SO_4$) and concentrated. The residue was purified by column chromatography ($SiO_2$, 90 g), being eluted with 30% EtOAc in hexane to obtain 255 mg (0.398 mmol, Y: 26.5%) of the starting silylether XVIIIa and 254 mg (0.483 mmol, Y: 32.2%) of the title compound, XIXa, as an oil: Rf 0.23 (50% EtOAc in hexane); IR (film) 3440 (OH), 1758 cm[1] (OAc); $^1$H-NMR (300 MHz, acetone-$d_6$) δ ppm: 1.46 (6H, s, gem-Me), 2.24 (3H, s, OAc), 2.25 (3H, s, Ar-Me), 2.48 (3H, s, Ar-Me), 3.28 (2H, t, J=5.2 Hz, OH), 3.44 (2H, m, $CH_2OH$), 5.12 (2H, s, $OCH_2Ph$), 5.15 (2H, s, $OCH_2Ph$), 6.66 (1H, s, Ar-H), 7.36 (10H, s, Ph-Hs); MS (isobutane-DCI) m/e 527 (MH+).

EXAMPLE 19

3-(2′-Acetoxy-5′-dibenzylphosphonooxy-4′6′-dimethyl)phenyl-3,3-dimethylpropionic acid (IXb)

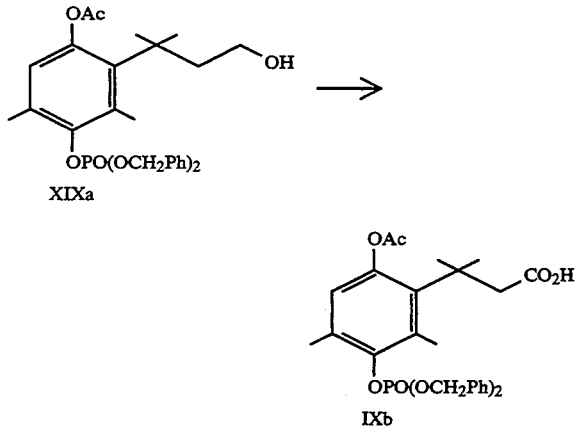

XIXa

IXb

To a solution of alcohol XIXa (250 mg, 0.47 mmol) in acetone (5 mL) was added at 0°–5° C. (ice-bath) Jones reagent (0.4 mL). The mixture was stirred for 30 min and the reaction was quenched by addition of isopropyl alcohol. To this green mixture was added EtOAc and $H_2O$. The aqueous phase was extracted with EtOAc (15 mL×3). The EtOAc extracts were combined, successively washed with $H_2O$ (15 mL) and brine (15 mL), dried ($Na_2SO_4$), and concentrated to obtain 226 mg (0.419 mmol, crude yield 89%) of the title compound as a crude oil. A portion of this oil (53 mg) was purified by column chromatography ($SiO_2$, 8 g), being eluted with 50% EtOAc in $CH_2Cl_2$ to obtain 24 mg (0.044 mmol, Y: 40%) of the title compound, IXb, as an oil: Rf 0.17 (20% EtOAc in $CH_2Cl_2$); IR (film) ~3000 (broad), 1758 (OAc) , 1728 $cm^{-1}$ ($CO_2H$); $^1$H-NMR (300 MHz, $CDCl_3$) δ ppm: 1.54 (6H, s, gem-Me), 2.23 (3H, s, Ar-Me), 2.27 (3H, s, OAc), 2.45 (3H, s, Ar-Me), 2.79 (2H, s, $CH_2$), 5.03 ( 2H, s, $OCH_2Ph$) , 5.06 ( 2H, s, $OCH_2Ph$) , 6.57 ( 1H, s, Ar-H), 7.25–7.33 (10H, m, Ph-Hs); MS (isobutane-DCI) m/e 541 (MH+), 481 (MH-HOAc).

EXAMPLE 20

1-t-Butyldimethylsilyloxymethyl-2-hydroxymethylbenzene (XXIa)

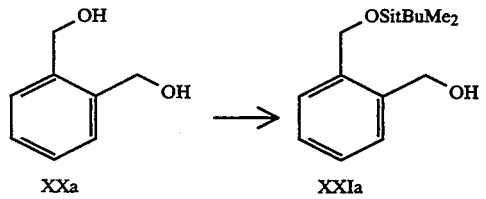

XXa XXIa

The following silylation was performed using the condition reported by Corey and Venkateswarlu. *J. Am. Chem. Soc.*, 94, 6190 (1972). A mixture of the diol (1.38 g, 10 mmol; Aldrich), t-butyldimethyl silyl chloride (1.81 g, 12 mmol; Aldrich) and imidazole (1.7 g, 25 mmol) in anhydrous DMF (10 mg; Aldrich Sure Seal) was stirred at room temperature for 18 h. To the mixture was added EtOAc (15 mL) and $H_2O$ (15 mL). The EtOAc phase was washed with $H_2O$ (15 mL×2) and then with brine, dried ($Na_2SO_4$), and concentrated in vacuo. The crude residue was purified by column chromatography ($SiO_2$, 100 g) , being eluted with 20% EtOAc in hexanes to obtain 1.018g (4.04 mmol, Y: 40.4%) of the title compound as a clear oil: Rf 0.53 (30% EtOAc in hexane); IR (film) 3380 $cm^{-1}$ (OH); $^1$H-NMR (300 MHz, acetone-$d_6$) δ ppm: 0.10 (6H, s, $SiMe_2$), 0.92 (9H, s, SitBu), 4.05 (1H, t, J=5.7 Hz, OH), 4.67 (2H, d, J=5.5 Hz, $CH_2OH$, 4.84 (2H, s, $CH_2OSi$), 7.24 (2H, m, ArHs), 7.42 (2H, m, ArHs); MS (isobutane-DCI) m/e 253 ($MH^+$), 235, 121.

Anal. calcd for $C_{14}H_{23}O_2Si$: C, 66.88; H, 9.22.

Found: C, 66.59; H, 9.58.

EXAMPLE 21

1-(Bisallylphosphonooxy)methyl-2-(t-butyldimethylsilyloxy)methylbenzene (XXIIa)

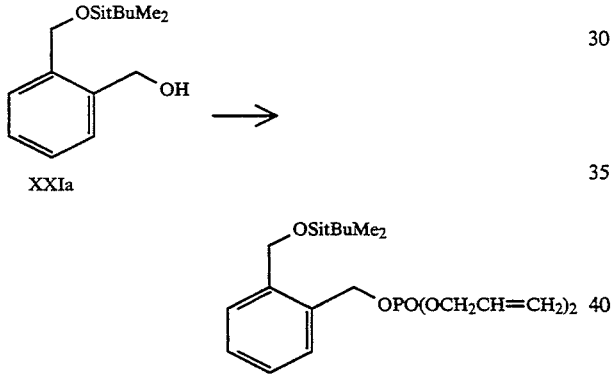

XXIa

XXIIa

To a solution of the siloxymethylbenzylalcohol XXIa (252 mg, 1 retool) in $CH_2Cl_2$ (10 mL; Aldrich Sure Seal) was added 1H-tetrazole (210 mg, 3 mmol; Aldrich) and then bis(allyloxy)(diisopropylamino)phosphine (520 mg, 1.5 mmol; prepared by the method of Bannwarth, *Tet. Lett.*, 30, 42 19 ( 1989 ) ) at room temperature. The mixture was stirred under nitrogen atmosphere at room temperature for 4 h. The mixture was cooled to −40° C. and to this mixture was added at −40° C. a solution of m-chloroperbenzoic acid (240 mg, 1.11 mmol; Aldrich, 80–85%) in $CH_2Cl_2$ (3 mL). The resulting mixture was stirred at 0–5° C. for 1 h and washed successively with aqueous $NaHSO_3$, saturated $NaHCO_3$ and brine, dried ($Na_2SO_4$), and concentrated. The residue was purified by column chromatography ($SiO_2$, 40 g), being eluted with 30% EtOAc in hexanes to obtain 269 mg (0.655 mmol, Y: 65.5%) of the title compound as a colorless oil: Rf 0.35 (30% EtOAc in hexane); 1H-NMR (300 MHz, acetone$d_6$) δ ppm: 0.126 (6H, s, $SiMe_2$), 0.957 (9H, s, tBu), 4.53 (4H, m, $OCH_2C$=), 5.16 (2H, s, $CH_2OSi$), 5.2 (4H, m, =$CH_2$ and $CH_2OP$), 5.36 (2H, bd, J=17 Hz, =$CH_2$), 5.95 (2H, m, CH=), 7.3–7.5 (4H, m, Ar-Hs); MS (isobutane-DCI) m/e 413 ($MH^+$).

Anal. calcd for $C_{20}H_{33}OsPSi$: C, 58.23; H, 8.06; P, 7.51.

Found: C, 58.03; H, 8.05; P, 7.50.

EXAMPLE 22

2-[(Bisallylphosphonooxy)methyl]benzyl alcohol (XXIIIa)

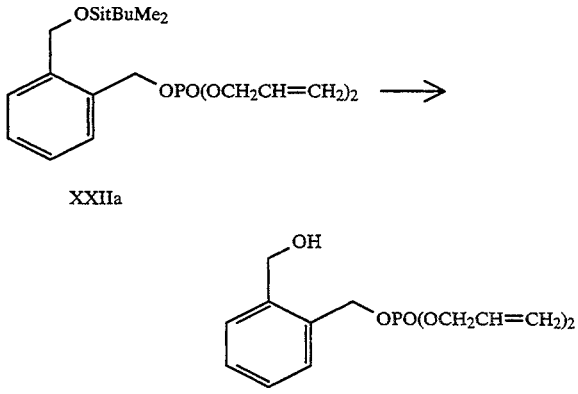

XXIIa

XXIIIa

To a solution of the silylether XXIIa (2.06 g, 5.00 mmol) in isopropanol (30 mL) was added 6N HCl (2.0 mL, 12 mmol) and the mixture stirred at room temperature for 3 h. The solvent was evaporated in vacuo without heat and the residue was diluted with EtOAc. This mixture was washed with $H_2O$ (×2), brine and dried ($Na_2SO_4$). Evaporation of the solvent gave a crude oil which was purified by column chromatography ($SiO_2$, 100 g), being eluted with 50% EtOAc in $CH_2Cl_2$ to obtain 1.33 g (4.46 mmol, Y: 89.2%) of the title compound as a colorless oil: Rf 0.3 (50% EtOAc in $CH_2Cl_2$); IR (film) 3406 (OH), 1264 $cm^{-1}$; $^1$H-NMR (300 MHz, acetone-$d_6$) δ ppm 4.26 (1H, t, J=5.5 Hz, OH), 4.51 (4H, m, $OCH_2$), 4.74 (2H, d, J=5.2 Hz, $CH_2OH$), 5.15–5.22 (4H, m, $CH_2OP$ and =$CH_2$) , 5.32 (2H, qd, J=1.5, 17.2 Hz, =$CH_2$), 5.85–6.01 (2H, m, CH=), 7.29–7.48 (4H, m, ArHs); MS (isobutane-DCI) m/e 299 ($MH^+$), 281, 179.

Anal. calcd for $C_{14}H_{19}OsP$: C, 56.38; H, 6.43.

Found: C, 56.21; H, 6.44.

EXAMPLE 23

2-[(BisallylphQsphonooxy)methyl]benzoic acid (IXc)

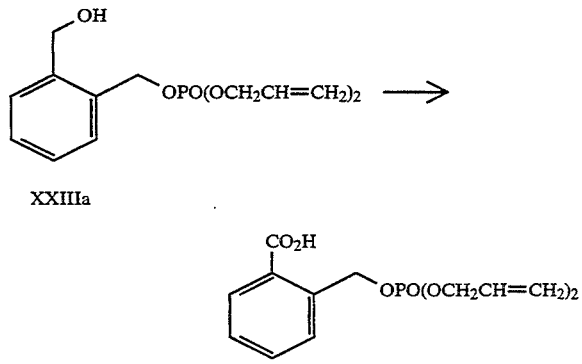

XXIIIa

IXc

To a solution of the benzylalcohol XXIIIa (1.31 g, 4.40 retool) in acetone (30 mL) was added at room temperature Jones reagent (3 mL). The mixture was stirred at room temperature for 0.5 h and the reaction was quenched by addition of i-PrOH (0.5 mL). To this green colored mixture was added EtOAc (50 mL) and then $H_2O$ (30 mL). The mixture was stirred to obtain a clear two-phase solution. The aqueous phase was extracted with EtOAc ( 20 mL) . The organic phases were combined, washed with $H_2O$ (×2) and brine, dried ($Na_2SO_4$), and concentrated to dryness in vacuo to obtain 1.347 g (4.32 retool, Y: 98.1%) of the title compound as a viscous oil: Rf 0.18 (EtOAc); IR (film) ~3000 ($CO_2H$), 1712 ($CO_2H$), 1260, 1226 $cm^{-1}$; $^1$H-NMR (300 MHz, $CDCl_3$) δ ppm 4.61 (4H, m, $OCH_2$), 5.24 (2H, dd, J=1.2, 10.5 Hz, =$CH_2$), 5.36 (2H, qd, J=1.5, 17.1 Hz, =$CH_2$), 5.66 (2H, d, J=6.9 Hz, $CH_2OP$), 7.38 (1H, t, J=7.3 Hz, 4-H), 7.57 (1H, t, J=7.6 Hz, 4-H), 7.69 (1H, d, J=7.8 Hz, 3-H), 8.07 (1H, dd, J=1.3, 7.7 Hz, 6-H); MS (isobutane-DCI) m/e 313 (MH+), 179, 135.

Anal. calcd for $C_{14}H_{17}O_6P$: C, 53.85; H, 5.49. Found C, 53.63; H, 5.50.

EXAMPLE 24

1-(Dibenzylphosphonooxy)-4-(t-butyldimethylsilyloxy)butane (XXVIIIa).

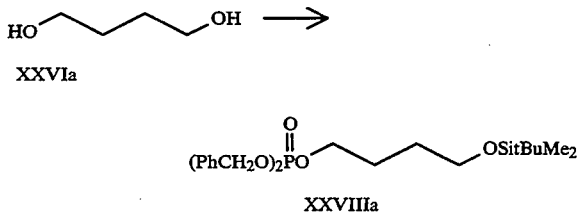

A solution of 1,4-butanediol (10.54 g, 0.117 mol) in dry THF (100 mL) was treated with t-butyl dimethylsilylchloride (17.30 g, 0.114 mol) and imidazole (7.80 g, 0.114 mol). After 2 h at room temperature, work-up with ethyl acetate and water, followed by drying the organic phase and concentration, gave a crude product that was purified by silica gel flash-chromatography (being eluted with 20% ethyl acetate in hexane) to yield 15.5 g (Y: 65%) of the title product as a colorless oil; $^1$H-NMR ($CDCl_3$, 300 MHz) δ 3.58 (m, 4H) 1.58 (m, 4H) 0.84 (s, 9H) 0.01 (s, 6H).

This oil (171.1 mg, 0.908 mmol) in dry dichloromethane (10 mL) was treated with dibenzyloxy(diisopropylamino)phosphine [prepared as in Bannwarth, W.; Trzeciak, A. Helv. Chim. Acta, 70, p. 175 (1987)] (399 mg, 1.120 mmol) and 1H-tetrazole (191 mg, 2.270 mmol). After 3 h at room temperature the suspension was cooled to −40° C., and solid m-chloroperbenzoic acid (50–60%, 570 mg, 1.82 mmol) was added. After 1 h the temperature of the mixture reached 0° C. Work-up with ethyl acetate and 5% aqueous sodium bicarbonate solution gave a crude product that was purified by silica gel flash chromatography (being eluted with 25% ethyl acetate in hexane) to yield the title compound as a yellow oil (185 mg, Y: 45%); $^1$H-NMR ($CDCl_3$, 300 MHz) ≧ 7.40–7.26 (m, 10H) 5.00 (m, 4H) 4.01 (q, 2H) 3.57 (t, 2H) 1.72–1.47 (m, 4H) 0.87 (s, 9H) 0.02 (s, 6H).

HRMS calcd for MH+: 465.2226, found: 465.2216.

EXAMPLE 25

4-(Dibenzylphosphonooxy)-1-butanol (XXIXa)

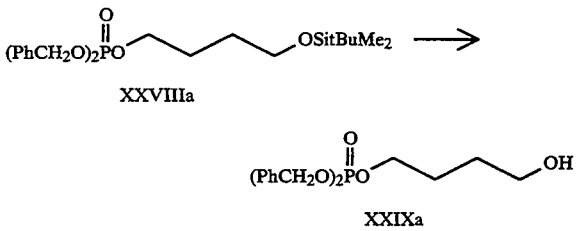

Silylated phosphate XXVIIIa (90 mg, 0.201 mmol) in dry THF (1 mL) was treated with tetrabutylammonium fluoride (1M in THF, 0.4 mL, 0.4 mmol). After 3 h at room temperature, the mixture was partitioned between water and EtOAc, dried, and loaded on a silica gel flash-column (being eluted with 40% ethyl acetate in hexane with 2% methanol) to give the title compound as an oil, 64.4 mg (Y: 92%); $^1$H-NMR ($CDCl_3$, 300 MHz) δ 7.38–7.28 (m, 10H) 5.01 (m, 4H) 4.02 (q, 2H) 3.59 (t, 2H) 1.73–1.51 (m,4H).

HRMS calcd for MH+: 351.1361, found: 351.1371.

EXAMPLE 26

4-(Dibenzylphosphonooxy)butanoic acid (XXVa)

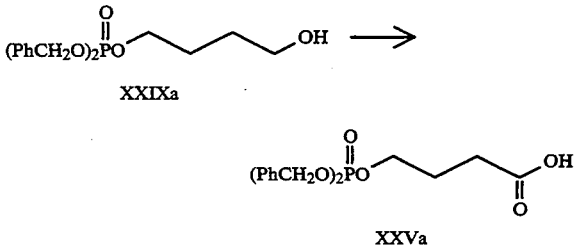

Alcohol XXIXa (772 mg, 2.200 mmol) in acetone (6 mL) at 0° C. was treated with chromic acid (Jones' reagent, 2.7 M, 4.15 mL, 11 mmol). After 16 h at room temperature, the mixture was diluted with water and extracted with ethyl acetate. The organic layer was washed with 10% aqueous sodium thiosulfate, dried and concentrated to yield the title compound as a colorless oil (746.8 mg, Y: 93%). This oil was used directly in a subsequent step without further purification; $^1$H-NMR ($CDCl_3$, 300 MHz) δ 7.53–7.27 (m, 10 H) 4.99 (m, 4H) 3.97 (q, 2H) 2.31 (t, 2H) 1.84 (m, 2H).

HRMS calcd for MH+: 365.1154. Found 365.1132.

EXAMPLE 27

4-Chlorobenzoic anhydride(XXXVa)

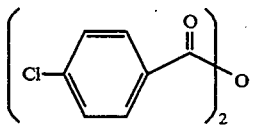

To a solution of 4-chlorobenzoic acid (34.0 g, 0.2 mol) in dry tetrahydrofuran (250 mL) was added dicyclohexylcarbodiimide (44.0 g, 0.22 mol). The mixture was stirred at room temperature for 18 h. It was diluted with dry ether to a volume of 1 liter and stirred at room temperature for an additional 30 min. Filtration of the mixture gave 26.0 g of a white solid (Y: 40%). The mother liquor was evaporated to dryness to give 30.0 g of a solid which was a mixture of the starting material and the product. This was purified by silica gel chromatography by eluting with methylene chloride and 10% acetonitrile in methylene chloride to give an additional amount of the title product; IR (KBr) 3432, 3066, 1728, 1644, $cm^{-1}$.

EXAMPLE 28

2'-(4-Chloromethylbenzoate) taxol (XXXa)

Method A

To a cold solution (−30° C.) of taxol (0.69 g, 0.8089 mmol) in dry tetrahydrofuran (30 mL) was added freshly prepared 0.1 M lithium diisopropylamide (LDA) solution (12.0 mL, 1.2 mmol). The mixture was stirred at −30° C. for 30 min. Then 4-chloromethylbenzoic anhydride (XXXVa) (0.39 g, 1.2 mmol) was added as solids and the resulting mixture was stirred at −30° C. for 4 h. It was treated with brine and ethyl acetate and the layers were separated. The aqueous layer was re-extracted with ethyl acetate, and the combined organic layers were dried (MgSO4) and evaporated to dryness to give a white foam. This was purified by silica gel chromatography (being eluted with methylene chloride and 10% and 20% acetonitrile in methylene chloride) to give 0.6 g (Y: 74%) of the title product; IR (KBr) 3432, 3066, 1728 1644, 1612, 1580, 1526, 1486, 1452, 1416, $cm^{-1}$; MS (FAB) MH+ m/z 1006, (M+Na)+ m/z 1028; $^1$H-NMR ($CDCl_3$) δ 1.074 (s, 3H), 1.206 (s, 3H), 1.653 (s, 3H), 1.737–1.904 (m, H), 1.938 (s, 3H), 2.099–2.120 (m, H), 2.201 (s, 3H), 2.270–2.321 (m, H), 2.419 (s, 3H), 2.483–2.587 (m, H), 3.793 (d, H), 4.165 (d, H), 4.288 (d, H), 4.485 (m, H), 4.586 (s, 2H), 4.948 (d, H), 5.655 (m, 2H), 6.017 (dd, H), 6.22 (t, H), 6.272 (S, H), 7.00 (d, H), 7.29–8.10 (m, 19H).

Method B

A mixture of DMAP (0.366 g, 3.0 mmol), DCC (0.93 g, 4.5 mmol) and 4-chloromethylbenzoic acid (0.78 g, 4.5 mmol) in dry $CH_2Cl_2$ (50 mL) was stirred at room temperature for 30 min. Taxol (2.50 g, 3.0 mmol) was added as solids and the mixture was stirred at room temperature for 18 h. The mixture was concentrated to dryness; the residue was triturated with acetone; and the insoluble material was filtered. The acetone filtrate solution was concentrated and the residue was purified on a silica gel column (being eluted with $CH_2Cl_2$ and 10%, 20% and 30% $CH_2Cl_2$ in $CH_3CN$) to give 1.80 g (Y: 60%) of the title compound. Spectral data were consistent for the compound.

Method C

To a cooled (5° C.) solution of taxol (0.43 g, 0.5 mmol) in dry $CH_2Cl_2$ (20 mL) was added N, N-diisopropylethylamine (0.5 ml) followed by a dropwise addition of 4-chloromethylbenzoyl chloride (0.19 g, 1.0 mmol) in dry $CH_2Cl_2$ (2 mL). The resulting mixture was stirred at 5°–15° C. for 3 h. It was washed with saturated aqueous $NaHCO_3$ solution and brine. It was dried ($MgSO_4$) and concentrated to give a solid residue. The residue was purified on a silica gel plate (being eluted with $CH_2Cl_2$: 30% $CH_3CN$) to give 0.5 g of the title product (Y: 100%).

EXAMPLE 29

General Preparation of Various 2'-[(N-substituted-4-Aminomethyl)benzoate]taxol Derivatives ($I^1$)

To a solution of a compound of formula XXX (1 equivalent) in acetone (10–20 mL) was added NaI (0.1 equivalent). This mixture was stirred at room temperature for 30 min. Then an appropriate amine (2–20 equivalents) was added, and the mixture was stirred at room temperature for 1 to 2 days. The reaction mixture was filtered over Celite and evaporated to dryness to give a free base as a foam. This foam was purified on a silica gel column, normally being eluted with methylene chloride and 2% to 10% methanol in methylene chloride to give the desired product.

Specific Examples

2'-[4-(Diethylaminomethyl)benzoate]taxol ($I^1$a)

To a solution of compound XXXa (0.1 g; 0.1 mmol) in acetone (10 mL) was added NaI (20 mg). The resultant mixture was stirred at room temperature for 15 min followed by addition of diethylamine (14.6 mg; 0.002 mL; 0.2 mmol). The mixture was stirred at room temperature for 18 h and evaporated to dryness. The residue was purified on silica gel preparative plates (being eluted with 10% MeOH in $CH_2Cl_2$) to give 73 mg (Y: 73%) of the title product.

The free base was dissolved in acetone and treated with one mole equivalent of L-tartaric acid. This solution was concentrated and treated with dry ether to give an L-tartaric acid salt of the title compound as a white solid; mp 176°–180° C. (decomposition); IR (KBr) 3450, 3064, 2970, 1728, 1670, 1610, 1582, 1484, 1452 $cm^{-1}$; MS (FAB) MH+ m/z 1043, (M+Na)+ m/z 1043; $^1$H-NMR ($CDCl_3$) δ 1.065 (t, 6H), 1.124 (s, 3H), 1.224 (s, 3H), 1.672 (s, 3H), 1.879 (m, H), 1.962 (s, 3H), 2.147 (m, H), 2.223 (s, 3H), 2.327 (m, H), 2.433 (s, 3H), 2.553 (m, 5H), 3.655 (m, 2H), 3.799 (d, H), 4.201 (d, H), 4.325 (d, H), 4.447 (m, H), 4.956 (d, H), 5.672 (m, 2H), 6.028 (m, H), 6.266 (t, H), 6.288 (s, H), 7.052 (d, NH), 7.20–8.20 (m, 19H).

HRMS Calcd. for MH+: 1043.4541. Found: 1043.4517.

2'-[4-(Morpholinomethyl)benzoate]taxol ($I^1$b)

To a solution of compound XXXa (0.2 g; 0.2 mmol) in acetone (10 mL) was added NaI (20 mg). This mixture was stirred at room temperature for 15 min, followed by addition of morpholine (35 mg; 0.04 mL; 0.4 mmol). The mixture was stirred at room temperature for 18 h and evaporated to dryness. The residue was purified on a silica gel column (being eluted with $CH_2Cl_2$ and 5% and 10% MeOH in $CH_2Cl_2$) to give the title product in a quantitative yield.

The free base was dissolved in acetone and treated with one mole equivalent of anhydrous citric acid. The solution was concentrated and diluted with dry ether to give a citric acid salt of the title compound as a beige solid; mp 170°–172° C.; IR (KBr) 3440, 3064, 2938, 2856, 1726, 1666, 1612, 1582, 1452, 1406, 1418, 1372 $cm^{-1}$; MS(FAB) MH+ m/z 1058, (M+K)+ m/z 1096; $^1$H-NMR ($CDCl_3$) δ 1.117 (s, 3H), 1.216 (s, 3H), 1.664 (s, 3H), 1.821 (m, H), 1.907 (S, 3H), 2.151 (m, H), 2.221 (s, 3H), 2.277 (m, H), 2.430 (s, 3H), 2.505 (m, 4H), 3.719 (m, 4H), 3.815 (d, H), 4.104 (d, H), 4.286 (d, H), 4.425 (m, H), 4.945 (d, H), 5.677 (m, 2H), 6.022 (m, H), 6.223 (t, H), 6.250 (S, H), 7.071 (d, NH), 7.200–8.200 (m, 19H).

HRMS Calcd. for MH+: 1057.4334. Found: 1057.4346.

2'-[4-[1-(Piperidinyl)methyl]benzoate]taxol ($I^1c$)

To a solution of compound XXXa (0.1 g; 0.1 mmol) in acetone (10 mL) was added NaI (20 mg). This mixture was stirred at room temperature for 15 min, followed by addition of piperidine (17 mg; 0.02 mL; 0.2 mmol). The mixture was stirred at room temperature for 18 h and evaporated to dryness. The residue was purified on silica gel preparative plates (being eluted with 10% MeOH in $CH_2Cl_2$) to give 54 mg (Y: 54%) of the title compound.

The free base was dissolved in 10% methanol in methylene chloride and treated with one equivalent of cold 1N HCl in dry ether. The mixture was concentrated and filtered to give a hydrochloride salt of the title compound as a yellow solid; mp. 170° C. (decomposition); IR (KBr) 3460, 2940, 1730, 1660, 1250 $cm^{-1}$; MS (FAB) MH+ m/z 1055; $^1$H-NMR ($CDCl_3$) δ 1.118 (s, 3H), 1.217 (s, 3H), 1.665 (m, 7H), 1.880 (m, H), 1.959 (s, 3H), 2.127 (m, H), 2.158 (S, 3H), 2.216 (s, 3H), 2.319 (m, H), 2.439 (s, 3H), 2.621 (m, 4H), 3.816 (d, H), 4.165 (d, H), 4.293 (d, H), 4.444 (m, H), 4.950 (d, H), 5.658 (m, 2H), 6.041 (m, H), 6.257 (t, H), 6.282 (s, H), 7.043 (d, NH), 7.200–8.200 (m, 19H) .

HRMS Calcd. for MH+: 1055. 4541. Found: 1055. 4514.

2'-[4-[(Diethanolamino)methyl]benzoate]taxol ($I^1d$)

To a solution of XXXa (0.41 g; 0.4075 mmol) in acetone (10 mL) was added NaI (20 mg). This mixture was stirred at room temperature for 15 min, followed by addition of diethanolamine (86 mg, 0.8150 mmol). The mixture was stirred at room temperature for 18 h and evaporated to dryness. The residue was purified on silica gel preparative plates (being eluted with 10% MeOH in $CH_2Cl_2$) to give 0.24 g (Y: 55%) of the title compound.

The free base was dissolved in acetone and treated with one mole equivalent of anhydrous citric acid. This mixture was concentrated and treated with dry ether to give a citric acid salt of the title compound as a white solid; mp 141°–144° C.; IR (KBr) 3438, 3064, 2944, 2898, 1726, 1660, 1610, 1582 $cm^{-1}$; MS (FAB) MH+ m/z 1075, (M+K)+ m/z 1113; $^1$H-NMR ($CDCl_3$) δ 1.118 (s, 3H), 1.211 (s, 3H), 1.659 (s, 3H), 1.894 (m, H), 1.948 (s, 3H), 2.129 (m, H), 2.203 (s, 3H), 2.306 (m, H), 2.431 (s, 3H), 2.257 (m, H), 2.693 (m, 4H), 3.648 (m, 4H), 3.781 (d, H), 4.158 (d, H), 4.305 (d, H), 4.418 (m, H), 4.937 (d, H), 5.687 (m, 2H), 6.041 (m, H), 6.239 (t, H), 6.286 (s, H), 7.216 (d, NH), 7.200–8.200 (m, 19H).

HRMS Calcd. for MH+: 1075.4440. Found: 1075.4430.

2'-[4-[(4-Methyl-1-piperazinyl)methyl]benzoate]taxol ($I^1e$)

To a solution of compound XXXa (0.33 g, 0.328 mmol) in acetone (10 mL) was added NaI (30 mg). This mixture was stirred at room temperature for 15 min followed by addition of N-methylpiperazine (0.33 g, 3.28 mmol, 0.37 mL). The mixture was stirred at room temperature for 18 h and evaporated to dryness. The residue was purified on a silica gel preparative plate (being eluted with 10% MeOH in $CH_2Cl_2$) to give 0.22 g (Y: 63%) of the title compound.

The free base was dissolved in acetone and treated with one mole equivalent of L-tartaric acid. This mixture was concentrated and treated with dry ether to give a tartaric acid salt of the title compound as a white solid; mp 160°–163° C.; IR (KBr) 3448, 3064, 3030, 1726, 1664, 1612, 1582, 1518 $cm^{-1}$; MS (FAB) MH+ m/z 1070, (M+Na)+ m/z 1092, (M+K)+ m/z 1108; $^1$H-NMR ($CDCl_3$) δ 1.085 (s, 3H), 1.156 ( s, 3H), 1.586 (s, 3H), 1.683 (m, H), 1.894 (s, 3H), 2.063 (m, H), 2.153 (s, 3H), 2.226 (s, 3H), 2.366 (s, 3H), 2.438 (m, 8H), 3.498 (s, 2H), 3.835 (d, H), 4.132 (d, H), 4.254 (d, H), 4.384 (m, H), 4.911 (m, H), 5.617 (m, 2H), 5.974 (m, H), 6.190 (t, H), 6.225 (S, H), 6.967 (d, NH), 7.200–8.200 (m, 19H).

HRMS Calcd. for MH+: 1070.4650. Found 1070.4676.

2'-[4-[[4-(2-Hydroxyethyl)-1-piperazinyl]methyl]benzoate]taxol ($I^1f$)

To a solution of compound XXXa (0.53 g; 0.5263 mmol) in acetone (30 mL) was added NaI (50 mg). This mixture was stirred at room temperature for 15 min followed by addition of 1-(2-hydroxylethyl)piperazine (0.137 g; 0.13 mL; 1.0536 mmol). The mixture was stirred at room temperature for 18 h and evaporated to dryness. The residue was purified by a silica gel preparative plate (being eluted with 10% MeOH in $CH_2Cl_2$) to give 0.5 g of the title compound (Y: 86%).

The free base was dissolved in acetone and treated with two mole equivalents of L-tartaric acid. This mixture was concentrated and treated with dry ether to give a tartaric acid salt of the title compound as a yellow solid; mp 170°–173° C.; IR (KBr) 3422, 3064, 2940, 2818, 1724, 1652, 1534 $cm^{-1}$; MS (FAB) MH+ m/z 1100, (M+K)+ m/z 1138; $^1$H-NMR ($CDCl_3$) δ 1.102 (s, 3H), 1.199 (s, 3H), 1.648 (s, 3H), 1.853 (m, H), 1.935 (s, 3H), 2.096 (m, H), 2.195 (s, 3H), 2.303 (m, H), 2.415 (s, 3H), 2.603–2.766 (m, 10H), 3.568 (S, 2H), 3.713 (m, 2H), 3.795 (d, H), 4.175 (d, H), 4.297 (d, H), 4.424 (m, H), 4.953 (d, H), 5.655 (m, 2H), 5.995 (m, H), 6.224 (t, H), 6.269 (S, H), 7.088 (d, NH), 7.200–8.200 (m, 19H).

HRMS Calcd. for MH+: 1100.4756. Found: 1100.4729.

2'-[4-[[4-(2-Hydroxyethyl)-1piperidinyl]methyl]benzoate]taxol ($I^1g$)

To a solution of compound XXXa (0.29 g; 0.2882 mmol) in acetone (20 mL) was added NaI (20 mg). This mixture was stirred at room temperature for 15 min followed by addition of 4-(2-hydroxyethyl)piperidine (56 mg, 0.4323 mmol). The mixture was stirred at room temperature for 18 h and evaporated to dryness. The residue was purified on silica gel preparative plates to give 0.32 g (quantitative yield) of the title compound.

The free base (0.32 g; 0.2914 mmol) was dissolved in acetone (10 mL) and treated with 0.1M L-tartaric acid in MeOH (2.9 mL; 0.29 mmol). This mixture was concentrated and treated with dry ether to give a tartaric acid salt of the title compound as a white solid; mp 178°–180° C.; IR (KBr) 3440, 3064, 3030, 2934, 2802, 1662, 1610, 1582, 1518, 1486, 1452, 1372 $cm^{-1}$; MS (FAB) MH+ m/z 1099, (M+Na)+ m/z 1121, (M+K)+ m/z 1137; $^1$H-NMR ($CDCl_3$) δ 1.119 (s, 3H), 1.217 (s, 3H), 1.518 (m, 7H), 1.667 (s, 3H), 1.873 (m, H), 1.957 (s, 3H), 2.111 (m, H), 2.215 (s, 3H), 2.316 (m, H), 2.432 (s, 3H), 2.597 (m, H), 2.875 (m, 2H), 3.684 (m, 2H), 3.816 (d, H), 4.196 (d, H), 4.370 (d, H), 4.440 (m, H), 4.975 (d, H), 5.665 (m, 2H), 6.030 (m, H), 6.252 (t, H), 6.284 (S, H), 7.096 (d, NH), 7.200–8.700 (m, 19H) .

HRMS Calcd. for MH+: 1099.4804. Found 1099.4767.

2'-[4-[[2-S-(Hydroxymethyl)-1-pyrrolidinyl]methyl]-benzoate]taxol ($I^1h$)

To a solution of compound XXXa (0.29 g, 0.2882 mmol) in acetone (10 mL) was added NaI (20 mg). This mixture was stirred at room temperature for 15 min followed by addition of L-prolinol (44 mg, 0.042 mL, 0.433 mmol). The mixture was stirred at room temperature for 18 h, evaporated to dryness and purified on silica gel preparative plates to give 0.15 g (Y: 50%) of the title compound.

The free base (0.176 g, 0.1635 mmol) was dissolved in acetone (10 mL) and treated with one mole equivalent of L-tartaric acid in methanol (0.1M, 1.60 mL; 0.160 mmol). This mixture was concentrated and treated with dry ether and filtered to give 0.18 g of a tartaric acid salt of the the title compound; mp 150°–153° C.; IR (KBr) 3438, 3064, 2944, 1726, 1662, 1612, 1582, 1486 $cm^{-1}$; MS (FAB) MH+ m/z 1071, (M+Na)+ m/z 1093, (M+K)+ m/z 1109; $^1$H-NMR ($CDCl_3$) δ 1.112 (s, 2H), 1.218 (s, 3H), 1.705 (s, 3H), 1.804–2.116 (m, 6H), 2.221 (s, 3H), 2.373 (m, H), 2.441 (s, 3H), 2.545 (m, 3H), 3.454–3.697 (m, 4H), 3.794 (d, H), 4.170 (d, H), 4.320 (d, H), 4.445 (m, H), 4.951 (m, 2H), 5.671 (m, 2H), 6.026 (m, H), 6.250 (t, H), 6.287 (s, H), 7.098 (d, NH), 7.200–8.200 (m, 19H).

HRMS Calcd. for MH+: 1071.4491. Found 1071.4449.

2'-[4-[(N,N,N'-Trimethylethylenediamino)methyl]benzoate]taxol ($I^1i$)

To a solution of compound XXXa (0.5 g, 0.5 mmol) in acetone (20 mL) was added NaI (0.1 g). This mixture was stirred at room temperature for 15 min, followed by addition of N,N,N'-trimethylethylenediamine (51.09 mg, 0.064 mL, 0.5 mmol), stirred at room temperature for 18 h, and evaporated to dryness. The residue was purified on a silica gel preparative plate (being eluted with 10% MeOH in $CH_2Cl_2$) to give 0.24 g (Y: 45%) of the title compound.

The free base (0.2 g, 0.1867 mmol) was dissolved in acetone (2 mL) and methanol (1 mL) and treated with L-tartaric acid in methanol (0.1M, 3.72 mL, 0.372 mmol). This mixture was concentrated, treated with dry ether, and filtered to give an L-tartaric acid salt of the title compound as an ivory colored solid (Y: 0.14 g); mp 140°–143° C.; IR (KBr) 3432, 3062, 3030, 2944, 2816, 1724, 1660, 1610, 1580, 1486 $cm^{-1}$; MS (FAB) MH+ m/z 1072, (M+Na)+ m/z 1094; $^1$H-NMR ($CDCl_3$) δ 1.113 (s, 3H), 1.211 (s, 3H), 1.657 (s, 3H), 1.860 (m, H), 2.025 (s, 3H), 2.076 (m, 3H), 2.204 (s, 3H), 2.243 (s, 3H), 2.437 (s, 3H), 2.584 (m, H), 2.695 (s, 6H), 2.837 (m, 2H), 3.072 (m, 2H), 3.647 (s, 2H), 3.775 (d, H), 4.182 (d, H), 4.309 (d, H), 4.346 (m, H), 5.667 (m, 2H), 6.031 (m, H), 6.217 (t, H), 6.276 (s, H), 7.224 (d, NH), 7.200–8.200 (m, 19H).

HRMS Calcd. for MH+: 1072.4807. Found 1072.4767.

2'-[4-[(N,N,N'-Trimethyl, 1,3-propanediamino)methyl]benzoate]taxol ($I^1j$)

To a solution of compound XXXa (0.5 g; 0.5 mmol) in acetone (20 mL) was added NaI (0.1 g). This mixture was stirred at room temperature for 15 min followed by addition of N,N,N'-trimethyl-1,3-propanediamine (58.105 mg, 0.0733 mL, 0.5 mmol). The mixture was stirred at room temperature for 18 h and evaporated to dryness. The residue was purified on silica gel preparative plates (10% MeOH in $CH_2Cl_2$) to give 0.16 g (Y: 30%) of the title compound.

The free base (0.13 g, 0.1198 mmol) was dissolved in acetone (2 mL) and methanol (1 mL), and treated with L-tartaric acid in methanol (0.1M, 2.4 mL, 0.24 mmol). The mixture was concentrated, treated with dry ether and filtered to give an L-tartaric acid salt of the title compound (Y: 0.13 g); mp 161°–164° C.; IR (KBr) 3424, 3062, 2942, 2804, 2700, 1658, 1610, 1580, 1524, 1486 $cm^{-1}$; MS (FAB): MH+ m/z 1086, (M+K)+ m/z 1124; $^1$H-NMR ($CDCl_3$) δ 1.118 (s, 3H), 1.215 (s, 3H), 1.663 (s, 3H), 1.830–2.111 (m, 4H), 2.004 (s, 3H), 2.221 (s, 3H), 2.225 (s, 3H), 2.443 (s, 3H), 2.534 (m, 4H), 2.747 (s, 6H), 3.055 (m, 2H), 3.603 (s, 2H), 3.783 (d, H), 4.160 (d, H), 4.290 (d, H), 4.442 (m, H), 4.946 (d, H), 5.677 (m, 2H), 6.018 (m, H), 6.225 (t, H), 6.282 (s, H), 7.160 (d, NH), 7.200–8.200 (m, 19H).

HRMS Calcd. for MH+: 1086.4963. Found: 1086.4915.

EXAMPLE 30

2'-[4-(Dimethylamino)benzoate]taxol ($I^3a$)

A mixture of dimethylaminobenzoic acid (0.2 g, 1.2 mmol), DMAP (0.12 g, 1.0 mmol) and DCC (0.25 g; 1.2 mmol) in dry $CH_2Cl_2$ (30 mL) was stirred at room temperature for 15 min. To this mixture was added taxol (0.85 g, 1.0 mmol) in dry $CH_2Cl_2$ (5 mL) dropwise. The mixture was stirred at room temperature for 3 days and evaporated to dryness. The residue was purified on a silica gel preparative plate (being eluted with 20% CH3CN in $CH_2Cl_2$) to give 1.0 g (Y: 92%) of the title compound.

The free base was dissolved in acetone and treated with one mole equivalent of L-tartaric acid. The mixture was concentrated and treated with dry ether to give an L-tartaric acid salt of the title compound as a white solid; mp 175°–177° C.; IR (KBr) 3446, 3328, 3064, 2930, 1716, 1668, 1628, 1580 $cm^{-1}$; MS (FAB) MH+ m/z 1001, (M+Na)+ m/z 1023, (M+K)+ m/z 1039; $^1$H-NMR ($CDCl_3$) δ 1.112 (s, 3H), 1.217 (s, 3H), 1.658 (s, 3H), 1.922 (s, 3H), 2.092 (m, H), 2.215 (s, 3H), 2.429 (s, 3H), 2.536 (m, H), 3.058 (s, 6H), 3.799 (d, H), 4.184 (d, H), 4.302 (d, H), 4.440 (m, H), 4.962 (d, H), 5.650 (m, 2H), 5.949 (m, H), 6.233 (t, H), 6.270 (s, H), 6.632 (d, 2H), 7.175 (d, NH), 7.200–8.200 (m, 21H).

HRMS Calcd. for MH+: 1001.4072. Found: 1001.4061.

EXAMPLE 31

2'-[4-[[4-[2-(Phosphonooxy)ethyl]-1-piperazinyl]methyl]benzoate]taxol ($I^1k$)

To compound $I^1f$ (0.33 g, 0.3 m mol) in dry $CH_2Cl_2$ (20 ml) was added (at room temperature) diisopropylethylamine (0.5 ml) followed by bis(2,2,2-trichloroethyl)-phosphorochloridate (0.57 g, 1.5 mmol). The resulting mixture was stirred at room temperature under argon atmosphere for 3 h. It was washed with cold aqueous $NaHCO_3$ solution, water and brine, dried ($MgSO_4$), and concentrated to give a residue which was purified on a silica gel plate (being eluted with 10% MeOH in $CH_2Cl_2$) to give 0.25 g (Y: 58%) of 2'-[4-[[4-[2-[bis(2,2,2-trichloroethyl)phosphonooxy]ethyl]-1-piperazinyl]methyl]benzoate]taxol (XXXIa) as a foam. NMR ($CDCl_3$) δ: 1.10 (s, 3H), 1.20 (s, 3H), 1.65 (s, 3H), 2.0 (s, 3H), 2.20 (s, 3H), 1.80–2.40 (m, 3H), 2.4–2.8 (m, 8H), 3.5 (m, 2H), 3.80 (d, H), 4.15 (d, H), 4.30 (d, 3H), 4.40 (m, H), 4.60 (m, 2H), 4.90 (d, H), 5.65 (m, 2H), 6.0 (dd, H), 6.20 (t, H), 6.25 (s, H), 7.0 (d, NH), 7.20–8.20 (m, 19H).

Removal of 2,2,2-trichloroethyl groups from compound XXXIa affords the title compound. The removal may be effected with zinc in acetic acid/methanol.

EXAMPLE 32

2′-[4-[[[Bis(2-phosphonooxy)ethyl]amino]methyl]benzoate]taxol ($I^1m$)

To compound $I^1d$ (0.20 g; 0.19 retool) in dry $CH_2Cl_2$ (10 mL) was added at room temperature diisopropylethylamine (0.5 ml) followed by bis (2,2,2-trichloroethyl)phosphorochloridate (0.82 g, 2.16 mmol). The resulting mixture was stirred at room temperature under argon for 3 h. It was washed with cold aqueous $NaHCO_3$ solution, water and brine, dried and concentrated to give a residue which was purified on a silica gel plate (being eluted with 10% MeOH in $CH_2Cl_2$) to give 0.11 g (Y: 34%) of 2′-[4-[[[bis(2-phosphonooxy)ethyl]amino]methyl]benzoate]taxol, 2′-tetrakis(2,2,2-trichloroethyl) ester (XXXIb) as a foam. NMR ($CHCl_3$) δ: 1.15 (s, 3H), 1.20 (bs, 6H), 1.70 (s, 3H), 2.25 (bs, 6H), 1.6–2.4 (m, 3H), 2.45 (m, 2H), 2.95 (m, 4H), 3.50 (m, 2H), 3.80 (m, 4H), 4.15 (d, H), 4.20 (m, 3H), 4.60 (m, 6H), 5.0 (d, 5.70 (m, 2H), 6.0 (m, H), 6.20 (t, H), 6.25 (s, H), 7.0 (d, NH), 7.20–8.20 (m, 19H).

Removal of 2,2,2-trichloroethyl groups from compound XXXIb affords the title compound. The removal may be effected with zinc in acetic acid/methanol.

Table 1 below lists taxol derivatives whose specific syntheses are described in the Examples.

TABLE 1

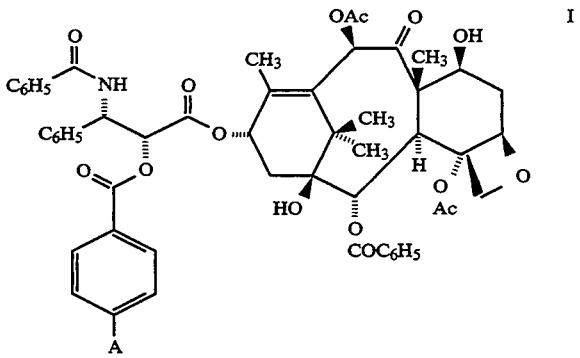

| COMPOUND # | A |
|---|---|
| $I^1a$ | 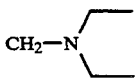 |
| $I^1b$ | 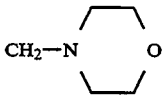 |
| $I^1c$ | 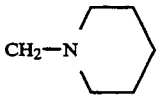 |

TABLE 1-continued

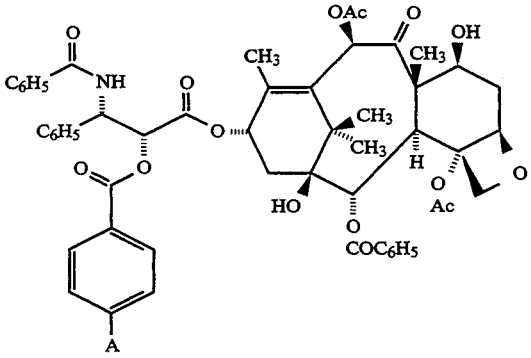

| COMPOUND # | A |
|---|---|
| $I^1d$ | 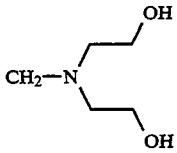 |
| $I^1e$ | 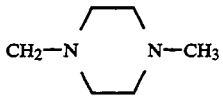 |
| $I^1f$ | 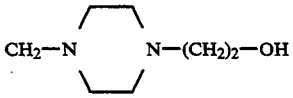 |
| $I^1g$ | 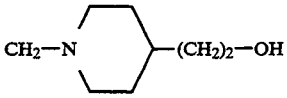 |
| $I^1h$ | 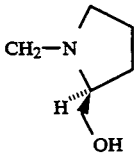 |
| $I^1i$ | 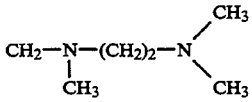 |
| $I^1j$ | 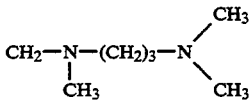 |
| $I^3a$ | 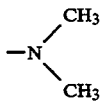 |
| XXXa | $CH_2Cl$ |
| $I^1k$ | 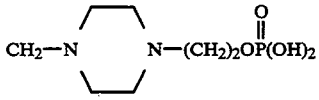 |

TABLE 1-continued

| COMPOUND # | A |
|---|---|
| I | 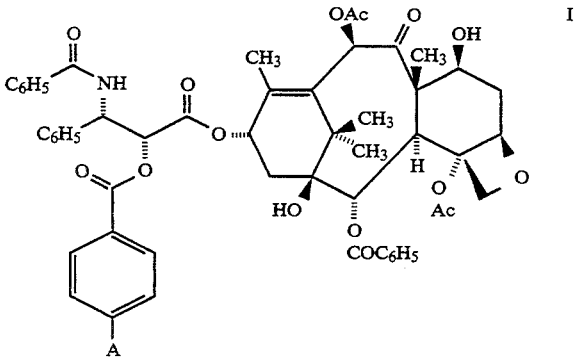 |
| $I^1m$ | 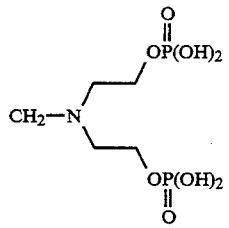 |
| XXXIa | 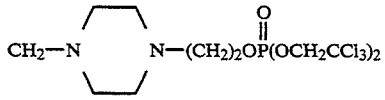 |
| XXXIb | 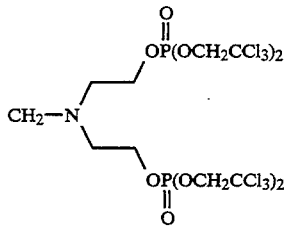 |

Biological Data

Mice M109 Model

Balb/c x DBA/2 $F_1$ hybrid mice were implanted intraperitoneally, as described by William Rose in *Evaluation of Madison* 109 *Lung Carcinoma as a Model for Screening Antitumor Drugs,* Cancer Treatment Reports, 65, No. 3–4 (1981), with 0.5 mL of a 2% (w/v) brei of M109 lung carcinoma.

Mice were treated with compound under study by receiving intraperitoneal injections of various doses on either Days 1, 5 and 9 post-tumor implant or Days 5 and 8 post-implant. Mice were followed daily for survival until approximately 75–90 days post-tumor implant. One group of mice per experiment remained untreated and served as the control group. Median survival times of compound-treated (T) mice were compared to the median survial time of the control (C) mice. The ratio of the two values for each compound-treated group of mice was multiplied by 100 and expressed as a percentage (i.e. % T/C) in Table 2 for certain representative compounds.

TABLE 2

| Compound | Maximum % T/C [Cures/Total] (dose in mg/kg/injection; schedule) |
|---|---|
| $I^1b$, citric acid salt | 259 (60; d. 1, 5 & 9) |
| $I^2d$, citric acid salt | >663 [5/6] (60; d. 1, 5 & 9) |
| $I^1e$, L-tartaric acid salt | 234 [1/6] (60; d. 1, 5 & 9) |
| $I^1f$, L-tartaric acid salt | 191 (160; d. 5 & 8) |
| $I^1g$, L-tartaric acid salt | 150 (160; d. 5 & 8) |
| $I^1h$, L-tartaric acid salt | 197 (160; d. 5 & 8) |
| $I^3a$, L-tartaric acid salt | 203 (80; d. 5 & 8) |
| $I^1i$, L-tartaric acid salt | 162 (45; d. 5 & 8) |
| $I^1j$, L-tartaric acid salt | 135 (160; d. 5 & 8) |

The foregoing test shows that the compounds of the instant invention have tumor inhibiting activities in mammals. Thus, another aspect of the instant invention concerns with a method for inhibiting mammalian tumors sensitive to a compound of formula I or a pharmaceutically acceptable salt thereof.

The present invention also provides pharmaceutical compositions (formulations) containing a compound of formula I in combination with one or more pharmaceutically acceptable, inert or physiologically active, carriers, excipients, diluents or adjuvants. Examples of formulating taxol or its related derivatives (including a possible dosage) are described in numerous literatures, for example in U.S. Pat. Nos. 4,960,790 and 4,814,470, and such examples may be followed to formulate the compounds of this invention. For example, the new compounds are administrable in the form of tablets, pills, powder mixtures, capsules, injectables, solutions, suppositories, emulsions, dispersions, food premix, and in other suitable forms. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50–500 mg. Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The mode, dosage and schedule of administration of taxol in human cancer patients have been extensively studied. See, for example Ann. Int. Med., ill, pp 273–279 (1989). For the compounds of this invention, the dose to be administered, whether a single dose, multiple dose, or a daily dose, will of course vary with the particular compound employed because of the varying potency of the compound, the chosen route of administration, the size of the recipient and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. The dosage to be administered will be generally in the range of 0.8 to 8 mg/kg of body weight or about 50–275 mg/m$^2$ of the patient. An oncologist skilled in the art of cancer treatment will able to ascertain, without undue experimentations, appropriate protocols for effective administration of the compounds of this present invention by referring to the earlier studies of taxol and its derivatives.

What is claimed:

1. A compound of formula I

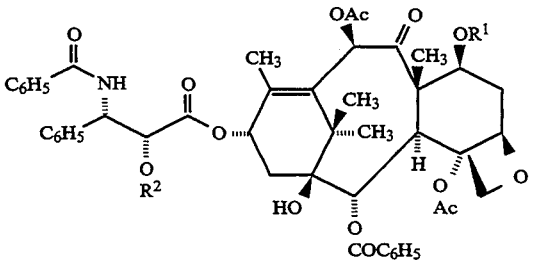

I or a pharmaceutically acceptable salt thereof, in which $R^2$ is a radical of the formula

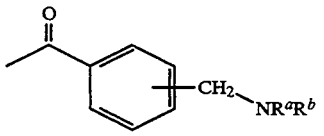

or

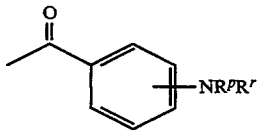

in which $R^a$ and $R^b$ are independently hydrogen or $C_{1-6}$ alkyl, said $C_{1-6}$ alkyl being optionally substituted with hydroxy, phosphono, phosphonooxy, carboxy or di($C_{1-6}$alkyl)amino; or $NR^aR^b$ together represents a radical of the formula

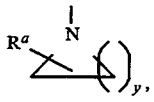

-continued

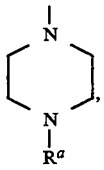

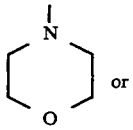

or

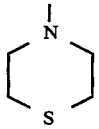

in which y is one to three, and $R^a$ is as defined above; $R^p$ and $R^r$ are independently same or different $C_{1-6}$ alkyl;

$R^1$ is hydrogen or a radical Z of the formula

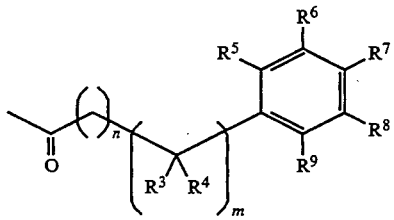

or

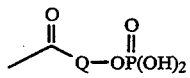

in which

Q is —$(CH_2)_f$—, optionally substituted with one to six same or different $C_{1-6}$ alkyl or $C_{3-6}$ cycloalkyl, or a carbon atom of said —$(CH_2)_f$— radical may also be a part of $C_{3-6}$ cycloalkylidene;

$R^3$ and $R^4$ are independently hydrogen or $C_{1-6}$ alkyl, or $R^3$ and $R^4$ taken together with the carbon atom to which they are attached form $C_{3-6}$ cycloalkylidene;

$R^5$ is —OC(=O)R, —OP=O$(OH)_2$ or —$CH_2$OP=O$(OH)_2$, in which R is $C_{1-6}$ alkyl;

$R^6$, $R^7$, $R^8$ and $R^9$ are independently halogen, $C_{1-6}$ alkyl, $C_{1-6}$ alkoxy or hydrogen, but when $R^5$ is —OC(=O)R, one of $R^6$, $R^7$, $R^8$ or $R^9$ is —OP=O$(OH)_2$; f is 2 to 6;

n is O, and m is 1 or 0 when $R^5$ is —$CH_2$OP=O$(OH)_2$; and n is 1 or 0, and m is 1 when $R^5$ is —OC(=O)R or —OP=O$(OH)_2$.

2. A compound as claimed in claim 1 in which $R^1$ is hydrogen; $R^a$ and $R^b$ are same or different $C_{1-6}$ alkyl, said $C_{1-6}$ alkyl being optionally substituted with hydroxy, phosphonooxy or di ($C_{1-6}$alkyl) amino, with the proviso that hydroxy or di($C_{1-6}$alkyl)amino is not attached to a carbon atom adjacent to nitrogen; or $NR^aR^b$ together represents a radical of the formula

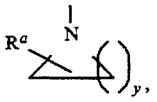

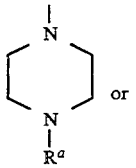

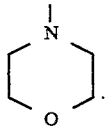

3. The compound of claim 2 that is 2′-[4-(diethylaminomethyl)benzoate]taxol.

4. The compound of claim 2 that is 2′-[4(morpholinomethyl)benzoate]taxol.

5. The compouud of claim 2 that is 2′-[4-[1-(piperidinyl)methyl]benzoate]taxol.

6. The compound of claim 2 that is 2′-[4-[[(diethanolamino)methyl]benzoate]taxol.

7. The compound of claim 2 that is 2′-[4-[(4-methyl-1-piperazinyl)methyl]benzoate]taxol.

8. The compound of claim 2 that is 2′-[4-[[4-(2-hydroxyethyl)-1-piperazinyl]methyl]benzoate]taxol.

9. The compound of claim 2 that is 2′-[4-[[4-(2-hydroxyethyl)-1-piperidinyl]methyl]benzoate]taxol.

10. The compound of claim 2 that is 2′-[4-[[2-S-(hydroxymethyl)-1-pyrrolidinyl]methyl]benzoate]taxol.

11. The compound of claim 2 that is 2′-[4- [(N,N,N′-trimethylethylenediamino)methyl]benzoate]taxol.

12. The compound of claim 2 that is 2′-[4-[(N,N,N′-trimethyl-1,3-propanediamino)methyl]benzoate]taxol.

13. The compound of claim 2 that is 2′-[4-(dimethylamino)benzoate]taxol.

14. The compound of claim 2 that is 2′-[4-[[4-[2-(phosphonooxy)ethyl]-1-piperazinyl]methyl]benzoate]taxol.

15. The compound of claim 2 that is 2′-[4-[[[bis(2-phosphonooxy)ethyl]amino]methyl]benzoate]taxol.

16. A pharmaceutical formulation which comprises as an active ingredient a compound as claimed in any one of claims 1 to 15, or a pharmaceutically acceptable salt thereof, associated with one or more pharmaceutically acceptable carriers, excipients or diluents therefor.

17. A method for treating mammalian tumors which comprises administering to a mammal a tumor sensitive amount of a compound as claimed in any one of claims 1 to 15.

* * * * *